US012290141B2

(12) United States Patent
Machanian

(10) Patent No.: US 12,290,141 B2
(45) Date of Patent: May 6, 2025

(54) INSOLE AND SYSTEMS INCLUDING SAME

(71) Applicant: ACTICS MEDICAL LTD, Rehovot (IL)

(72) Inventor: Ron Machanian, Rehovot (IL)

(73) Assignee: ACTICS MEDICAL LTD, Rehovot (IL)

( * ) Notice: Subject to any disclaimer, the term of this patent is extended or adjusted under 35 U.S.C. 154(b) by 170 days.

(21) Appl. No.: 18/040,367

(22) PCT Filed: Aug. 1, 2021

(86) PCT No.: PCT/IL2021/050927
§ 371 (c)(1),
(2) Date: Feb. 2, 2023

(87) PCT Pub. No.: WO2022/029761
PCT Pub. Date: Feb. 10, 2022

(65) Prior Publication Data
US 2023/0354952 A1    Nov. 9, 2023

Related U.S. Application Data

(60) Provisional application No. 63/167,663, filed on Mar. 30, 2021.

(30) Foreign Application Priority Data

Aug. 4, 2020  (IL) .......................................... 276498

(51) Int. Cl.
*A43B 3/44*    (2022.01)
*A43B 3/48*    (2022.01)
(Continued)

(52) U.S. Cl.
CPC .................. *A43B 3/44* (2022.01); *A43B 3/48* (2022.01); *A43B 7/38* (2013.01); *A61B 5/112* (2013.01)

(58) Field of Classification Search
CPC .... A43B 3/34; A43B 3/44; A43B 3/48; A43B 7/38; A61B 5/112
See application file for complete search history.

(56) References Cited

U.S. PATENT DOCUMENTS 5,797,201 A * 8/1998 Huang ..................... A43B 3/48
36/132
5,813,142 A * 9/1998 Demon .................... A43B 3/44
600/592

(Continued)

FOREIGN PATENT DOCUMENTS

CN    103961197    1/2016
EP    3389482      10/2018
(Continued)

OTHER PUBLICATIONS

Extended European Search Report issued in European Application No. 21853715.7, dated Sep. 4, 2024.

*Primary Examiner* — Heather Mangine
*Assistant Examiner* — Raquel M. Weis
(74) *Attorney, Agent, or Firm* — Benesch Friedlander Coplan & Aronoff LLP

(57) ABSTRACT

A system including: (a) an insole with a plurality of sensors and a plurality of adjustment mechanisms deployed thereupon at a plurality of locations, each sensor providing a data output signal; (b) a data processor receiving the data output signals from the sensors, analyzing data from the output signals and outputting a response plan; and (c) an implementation module receiving the response plan, translating the response plan to a plurality of response signals, and transmitting each response signal to a specific one of the plurality of adjustment mechanisms Additional systems and related insoles are also disclosed.

20 Claims, 18 Drawing Sheets

(51) Int. Cl.
*A43B 7/38* (2006.01)
*A61B 5/11* (2006.01)

(56) References Cited

U.S. PATENT DOCUMENTS

| | | | |
|---|---|---|---|
| 9,295,302 B1* | 3/2016 | Reed | A61H 3/00 |
| 9,603,416 B1* | 3/2017 | Walsh | A63B 21/0004 |
| 2004/0177531 A1* | 9/2004 | DiBenedetto | A43B 21/26 |
| | | | 36/132 |
| 2005/0183292 A1* | 8/2005 | DiBenedetto | A43B 13/187 |
| | | | 36/132 |
| 2007/0204687 A1* | 9/2007 | Haselhurst | A43D 1/025 |
| | | | 73/172 |
| 2008/0134541 A1* | 6/2008 | Bar-Haim | A61B 5/1038 |
| | | | 36/27 |
| 2010/0324455 A1 | 12/2010 | Rangel et al. | |
| 2013/0278436 A1* | 10/2013 | Ellis | A43B 13/20 |
| | | | 36/43 |
| 2014/0033572 A1* | 2/2014 | Steier | A61B 5/1038 |
| | | | 36/103 |
| 2014/0222173 A1* | 8/2014 | Giedwoyn | A43B 3/34 |
| | | | 700/91 |
| 2015/0068069 A1* | 3/2015 | Tran | G08B 21/023 |
| | | | 340/693.1 |
| 2016/0239014 A1* | 8/2016 | Piontkowski | A43B 13/145 |
| 2016/0249829 A1* | 9/2016 | Trabia | A61B 5/7246 |
| | | | 600/592 |
| 2016/0302521 A1* | 10/2016 | Rennex | A43B 13/184 |
| 2016/0345663 A1* | 12/2016 | Walker | A43B 7/24 |
| 2017/0071287 A1* | 3/2017 | Kim | A43C 15/09 |
| 2017/0071289 A1* | 3/2017 | Auyang | A43B 13/04 |
| 2017/0225033 A1* | 8/2017 | Czaja | A43B 3/34 |
| 2017/0340051 A1* | 11/2017 | Rogers | A43B 21/24 |
| 2018/0035752 A1* | 2/2018 | Walker | A43B 3/34 |
| 2019/0059511 A1* | 2/2019 | Walker | A43B 3/34 |
| 2019/0059514 A1* | 2/2019 | Walker | A43B 13/187 |
| 2019/0110551 A1* | 4/2019 | Walker | G01B 7/30 |
| 2019/0231578 A1 | 8/2019 | Ranganathan et al. | |
| 2019/0313913 A1* | 10/2019 | Fu | A61B 5/01 |
| 2020/0375310 A1* | 12/2020 | Weast | A43B 13/206 |
| 2023/0354952 A1* | 11/2023 | Machanian | A43B 7/147 |
| 2024/0156213 A1* | 5/2024 | Machanian | A61B 5/1038 |

FOREIGN PATENT DOCUMENTS

| | | | | |
|---|---|---|---|---|
| FR | 3088552 | | 6/2020 | |
| KR | 101323725 | | 10/2013 | |
| KR | 102016981 | B1 | 9/2019 | |
| WO | WO-2009019692 | A2 * | 2/2009 | A43B 13/145 |
| WO | 2019200148 | | 10/2019 | |
| WO | WO-2019200148 | A1 * | 10/2019 | A43B 3/0005 |
| WO | WO-2022029761 | A1 * | 2/2022 | A43B 3/44 |
| WO | WO-2022208496 | A1 * | 10/2022 | A43B 17/00 |

* cited by examiner

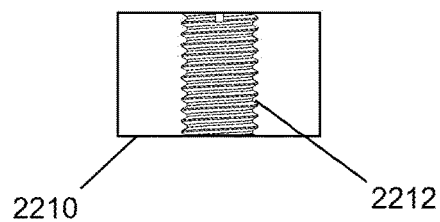
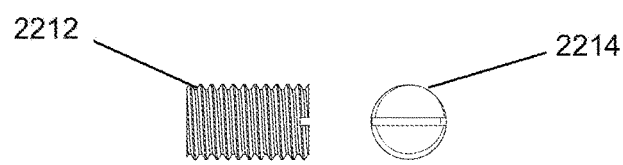
*Fig. 10A*  *Fig. 10B*  *Fig. 10C*
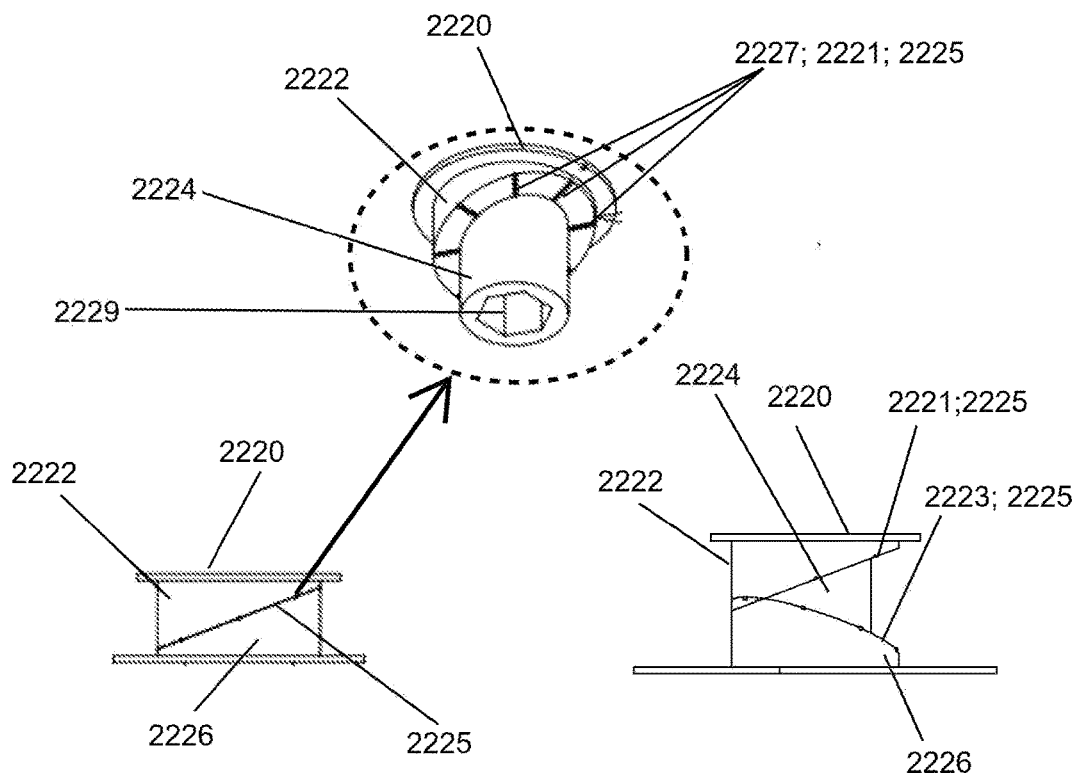
*Fig. 10D*  *Fig. 10E*

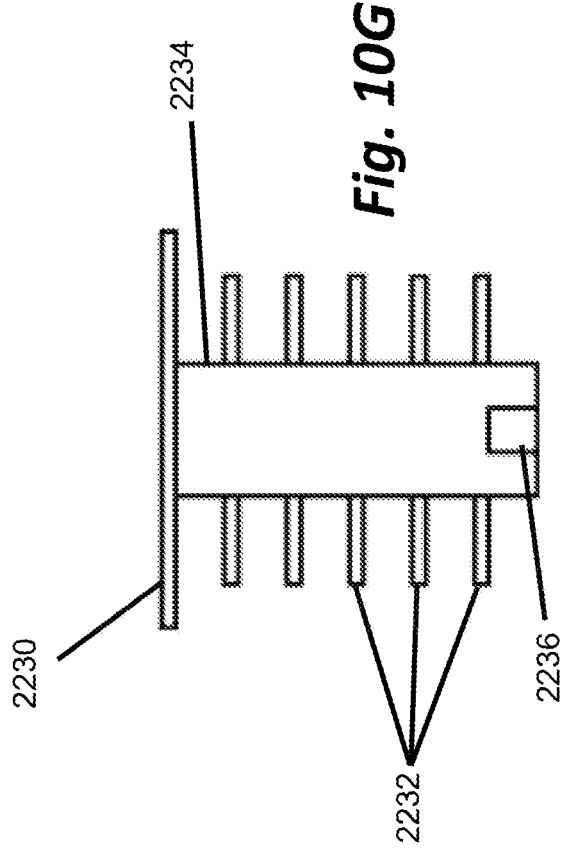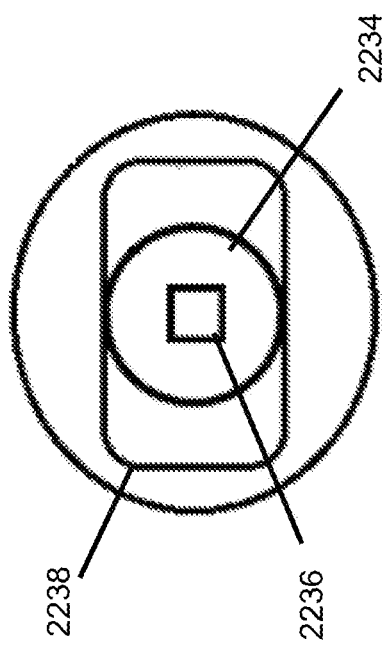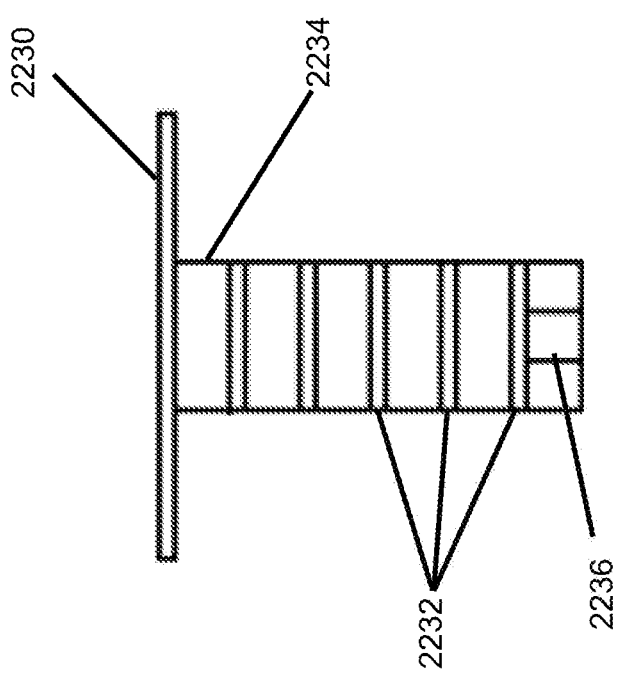

INSOLE AND SYSTEMS INCLUDING SAME

FIELD OF THE INVENTION

The invention is in the field of orthotics.

BACKGROUND OF THE INVENTION

Insoles are often present in footwear produced commercially and/or sold separately to add to shoes. The typical insole is a generic device made of foam rubber and/or cloth.

There are also commercially available unchanging "off the shelf" insoles featuring foam and/or gel and/or air cushions that purport to increase comfort if they are installed in shoes sold separately from the insole. These fixed passive insoles are generic devices that can't be adjusted to the user's personal anatomy or medical condition.

In addition, orthopedists, podiatrists, physiotherapists and other health professionals employ a variety of different personally customized fixed passive insole types for diagnosis, planning and treatment to address various symptoms, usually having to do with pain and discomfort of the feet and/or lower extremity. Conditions such as arthritis, back pain, foot deformities, Plantar fasciitis, heel injuries, Achilles injuries and ruptures, bone spurs, bunions, bursitis, pronation (flat feet), high arch, fractures, hammer toes, sarcopenia, balance impairments, elderly falls, foot inflammation, neuroma, lesions, osteoporosis, diabetic foot ulcers and tendonitis all cause pain. Sufferers from these maladies can't be treated with generic insoles, since they require a solution that fits their personal foot structure and/or condition.

Treatment planning in medical fields (e.g., orthopedics) or sport training is typically based on professional assessment, manual and/or digital. The assessment can include, besides a physical observation, video and/or computer monitoring of certain actions, in a static or dynamic manner such as standing, running or walking (e.g., in a gait lab). Alternatively, or additionally, the assessment can include evaluation of biomechanical function, the mobility of the foot and/or ankle and/or muscles and knees and/or hips. Muscles are typically evaluated with respect to tone and/or range of motion. Alternatively, or additionally, range of motion of each joint is evaluated.

Capturing reliable information about a person's gait in real-life environments remains challenging. Standard gait-analysis technologies, such as camera-based motion-capture systems and force plates, are expensive and can only be used inside laboratories, so they offer few insights into people biomechanical motion in the real world. However, existing insole products cannot provide accurate gait data nor accurate foot fit nor treatment. Based on the assessment, a treatment plan including orthopedic shoes and and/or customized insoles and/or orthotics (braces) may be proposed.

Unfortunately, custom-made orthotics have drawbacks. Since the result is a pair of fixed passive insoles, there is no way for online monitoring of the compatibility and quality of the solution, not to mention any dynamic adjustment. Although fit accuracy and compatibility of orthotics is crucial, they are not fitted reliably. Moreover, they are not adapted to the changes and fit accuracy drops with different physical activities, or with different articles of footwear or with trauma to foot or with natural states that happen in the body over time such as weight gain or loss, pains, or other disorders that affects our biomechanics and therefore to ineffective insoles and/or short product life that both patients and professionals can be unware to.

Diabetic foot ulcer (DFU) and accompanying lower extremity complications rank among the most debilitating and costly sequelae of diabetes in both the developed and developing world. Custom-made orthotic insoles have been shown to reduce plantar pressures in patients at risk of plantar ulceration. The recurrent trauma at pressure points on the sole increases the risk of local inflammation which manifests an elevated temperature at the affected site. Currently, temperature at different locations on the foot is measured manually.

Randomized controlled trials (RCT) and meta-analyses show that DFU is preventable by controlling key reversible risk factors such as elevated local temperatures indicative of inflammation and implementing appropriate medical management.

Unfortunately, in many cases assessment of DFU occurs only after the has progressed to the point where severe damage has occurred.

SUMMARY OF THE INVENTION

A broad aspect of some embodiments of the invention relates to early detection and/or intervention in a wide variety of foot and/or gait abnormalities.

One aspect of some embodiments of the invention relates to an insole that diagnoses, analyzes and corrects problems. In some embodiments the insole includes a plurality of sensors to gather data.

According to various exemplary embodiments of the invention the sensors include one or more of pressure sensors, motion sensors, levelling sensors, gyroscope, shear stress sensors, humidity sensors, temperature sensors and accelerometers. Alternatively, or additionally, in some embodiments the insole includes processing modules and/or a wireless data transmitting module and/or a memory and/or a battery and/or a system on chip. In some embodiments data generated by sensors is transmitted and/or analyzed by an application that enables a user and/or a remote expert to provide and/or activate a response plan. According to various exemplary embodiments of the invention the analysis is conducted by a data processor in the insole and/or by a data processor worn or carried by a user of the insole (e.g., smartphone, smartwatch or dedicated wearable device) and/or by a remote server. In some embodiments the insole includes an adjustment mechanism adapted to implement the response plan and customize insole shape by extending in the vertical direction. According to various exemplary embodiments of the invention, the adjustment mechanisms includes one or more of pistons, piezoelectric materials, motors, gears, bevel gears, worm-drive gears, spring loaded mechanisms and hydraulic actuators. In some embodiments the insole is built to perform an autonomous active on-line bi-directional process of diagnosis and therapeutic activity in real time.

Another aspect of some embodiments of the invention relates to a system that receives time stamped data outputs from a plurality of insole mounted sensors and stores the data in a database in conjunction with UIDs (unique identifiers) for users. In some embodiments the system also receives time stamped response plans and correlates them to the UIDS. In some exemplary embodiments of the invention, analysis of changes in sensor output over time in conjunction with intervening response plan permits evaluation of treatment efficacy of the response plan.

Yet another aspect of some embodiments of the invention relates to a system that receives user input defining a problem area on the sole of the foot. In some embodiments the user input is provided via a touch screen (e.g., on a smartphone and/or tablet and/or smartwatch). In some embodiments the user input is translated to a response plan by a data processor. According to various exemplary embodiments of the invention the translation is conducted by a data processor in the insole, by a data processor worn or carried by a user of the insole (e.g., smartphone, smartwatch, tablet or dedicated wearable device) or by a remote server. In some embodiments the insole includes a dynamic, on-line and/or real-time, adjustment mechanism adapted to implement the response plan.

Still another aspect of some embodiments of the invention relates to a system that is reliable in the long run, is easily switched and/or used with automatic adjustment/calibration mode between several articles of footwear controlled by programmable input of paired smart device (e.g., smartphone). In some embodiments one advantage of such a system is to diminish the need for more than one pair of costly custom orthotics for different footwear.

According to various exemplary embodiments of the invention the adjustment mechanism includes one or more of pistons, piezoelectric materials, motors, gears, bevel gears, worm-drive gears, screws, spring loaded mechanisms and hydraulic actuators.

Alternatively, or additionally, according to various exemplary embodiments of the invention the adjustment mechanism and/or sensors is made of various polymers and/or electroactive polymers and/or materials that have transformable properties and/or conductive properties.

Some exemplary embodiments of the invention, offer advantages in the medical field, such as considerably simplifying diabetics' day-to-day life. Alternatively or additionally, in some embodiments patients are empowered in self-care. In some embodiments, patient empowerment contributes to improved patient adherence. Alternatively or additionally, in some embodiments effective delivery of data from at risk patients for remote monitoring contributes to a reduction in access disadvantage in remote areas.

For instance, by allowing continuous monitoring of abnormal plantar parameters (e.g. pressure distribution and/or foot temperature and/or skin humidity) the system is able to in addition to relieve pressure by off-loading in response to early signs of potential ulceration and/or to assist in healing and and maintaining mobility in post DFU stages. Therefore, it could early detect and/or prevent and/or delay foot ulceration wounds and/or recurrence of DFUs for diabetic patients by dynamically and/or autonomously customizing insole fit to eliminate abnormal pressure points to promote healing or prevention as a treatment.

Still another aspect of some embodiments of the invention relates to manually adjustable height adjustment mechanisms installed in insoles. In some embodiments a plurality of such mechanisms are distributed across an area of the insole. According to various exemplary embodiments of the invention the mechanisms are positioned under the medial arch, metatarsals, and/or heel of the insole. According to various exemplary embodiments of the invention the mechanisms employ press nuts and/or screws and/or diagonal joint rotary lifts, and/or bayonet mounts (hereinafter, "the height adjustment mechanisms").

Another aspect of some embodiments of the invention relates to sensors deployed in an insole. According to various exemplary embodiments of the invention the sensors include pressure sensors, and/or temperature/climate sensors, and/or leveling sensors, and/or gyroscopes, and/or accelerometers.

Another additional aspect of some embodiments of the invention relates to a data processor which receives output signal data from sensor(s) in an insole and provides user alerts and/or advice in response to the data. According to various exemplary embodiments of the invention the data processor is incorporated into the insole or located externally. In some embodiments an internal and an external data processor operate cooperatively. In some embodiments the user advice includes instructions for manual adjustment of individual height adjustment mechanisms in the insole. Alternatively, or additionally, in some embodiments the user advice includes an alert concerning a nascent foot ulcer and/or an orthopedic and/or biomechanics problem. In some exemplary embodiments of the invention, the diagnosis and/or the alert and/or the user advice is presented on a digital user interface (UI) of a smartphone, smartwatch, tablet or PC.

In some embodiments of the invention a correction and/or an adjustment plan can be initiated and/or implemented manually with "height adjustment mechanisms" either individually and/or by a machine learning algorithm advice plan based on diagnosis gathered from data collected by the sensors deployed in the insole.

It will be appreciated that the various aspects described above relate to solution of technical problems associated with early diagnosis and intervention in a wide variety of gait related and/or mobility and/or medical disorders.

Alternatively, or additionally, it will be appreciated that the various aspects described above relate to solution of technical problems related to providing symptomatic relief from foot pain and/or knee pain and/or hip pain and/or back pain and/or lower limb neuropathic pain (e.g. diabetic foot ulcers).

Alternatively, or additionally, it will be appreciated that the various aspects described above relate to early diagnosis, and/or evaluation and/or therapeutic measures for chronic foot maladies and pains (e.g. diabetic foot ulcers).

Alternatively or additionally, it will be appreciated that the various aspects described above relate to solution of technical problems associated with customization of orthotic devices.

Alternatively, or additionally, it will be appreciated that the various aspects described above relate to solution of technical problems related to early detection of nascent foot ulcers and/or other medical disorders and/or matters of improving gait and/or mobility capabilities.

In some exemplary embodiments of the invention there is provided a system including:

(a) an insole with a plurality of sensors and a plurality of adjustment mechanisms deployed thereupon at a plurality of locations, each sensor providing a data output signal; (b) a data processor receiving the data output signals from the sensors, analyzing data from the output signals and outputting a response plan; and (c) an implementation module receiving the response plan, translating it to a plurality of response signals, and transmitting each response signal of the plurality of response signals to a specific one of the plurality of adjustment mechanisms. In some embodiments the data processor outputs an alert signal. Alternatively or additionally, in some embodiments the sensors include at least one member of the group consisting of pressure sensors, temperature sensors, motion sensors, transducers, levelling sensors, gyroscopes and accelerometers. Alternatively or additionally, in some embodiments the data processor is located at least one member of the group consisting of in/on the insole, worn or carried by a user of the insole (e.g. smartphone, smartwatch or dedicated wearable device) and at a remote server. Alternatively or additionally, in some embodiments the adjustment mechanism includes at least one member of the group consisting of pistons, piezoelectric materials, motors, gears, bevel gears, worm-drive gears, spring loaded mechanisms hydraulic actuators, polymers and electroactive materials. Alternatively or additionally, in some embodiments the system includes a stimulation module under control of said implementation module, wherein said response plan includes a stimulation signal. According to various exemplary embodiments of the invention the stimulation module includes at least one member of the group consisting of a physical stimulator, a laser, vibrator and a source of electric current.

In some exemplary embodiments of the invention there is provided a system including: (a) a plurality of insoles equipped with sensors producing time stamped data output signals labeled with UIDs (unique identifiers) for users; and (b) a database receiving and storing the time stamped data output signals labeled with UIDs. In some embodiments the system includes one or more data processors receiving the data output signals from the sensors, analyzing data from output signals correlated with a specific UID and outputting a UID specific response plan which is time stamped and stored; and a response plan delivery module transmitting the UID specific response plan to insoles associated with the UID.

In some exemplary embodiments of the invention there is provided a system including: (a) a user interface (UI) adapted to receive user input defining a problem area on the sole of a foot; and (b) a data processor including a translation module adapted to translate the user input into a response signal. In some embodiments the UI is provided via a touch screen. Alternatively or additionally, in some embodiments the data processor resides at at least one location selected from the group consisting of in an insole, worn/carried by a user of an insole and a remote server. Alternatively or additionally, in some embodiments the system includes an insole comprising an adjustment mechanism adapted to respond to the response signal; and a response signal delivery module adapted to transmit the response signal to the insole. Alternatively or additionally, in some embodiments the adjustment mechanism includes at least one member of the group consisting of pistons, piezoelectric materials, motors, gears, bevel gears, worm-drive gears, spring loaded mechanisms hydraulic actuators, polymers and electroactive materials. Alternatively or additionally, in some embodiments the system includes a stimulation module, responsive to the response signal. Alternatively or additionally, in some embodiments the stimulation module includes at least one member of the group consisting of a physical stimulator, a laser, a vibrator and a source of electric current.

In some exemplary embodiments of the invention there is provided an insole including: (a) a plurality of height adjustment mechanisms integrated across at least a portion of an area thereof; and (b) a manual adjustment interface for each of the height adjustment mechanisms. In some embodiments each of the height adjustment mechanisms is independently selected from the group consisting of a screw, a diagonal joint rotary lift, and a bayonet mount. Alternatively or additionally, in some embodiments the insole includes one or more sensors. Alternatively or additionally, in some embodiments each of the sensors is individually selected from the group consisting of a pressure sensor, a temperature/climate sensor, a leveling sensor, a gyroscope and an accelerometer. Alternatively or additionally, in some embodiments the insole includes a data communication channel configured to transmit an output signal from the one or more sensors to a data processor. Alternatively, or additionally, in some embodiments the insole includes the data processor. Alternatively or additionally, in some embodiments the insole includes a stimulation module and a manual activation interface for the stimulation module. Alternatively or additionally, in some embodiments the stimulation module includes at least one member of the group consisting of a physical stimulator, a laser, vibrator and a source of electric current.

In some exemplary embodiments of the invention there is provided a system including: (a) one or more insoles with a plurality of height adjustment mechanisms integrated across at least a portion of an area thereof and a manual adjustment interface for each of the height adjustment mechanisms; (b) one or more sensors in the one or more insoles providing one or more output signal(s); (c) a data processor designed and configured to translate the output signal(s) to advice; and (d) an interface presenting diagnosis and/or the advice. In some embodiments the data processor resides in a device external to the insoles. Alternatively or additionally, in some embodiments the device external to the insole is selected from the group consisting of a smartphone, smartwatch, a PC (personal computer) and a tablet. Alternatively or additionally, in some embodiments the system includes a wireless communication link between the sensors and the data processor. Alternatively or additionally, in some embodiments the user advice includes a set of instructions for manual adjustment of each of the height adjustment mechanisms.

Alternatively, or additionally, in some embodiments the user advice includes an alert concerning a nascent foot ulcer. Alternatively, or additionally, in some embodiments the clinical data collected is used to measure patient adherence and to enable remote continuous monitoring and/or connected care. With this continuity of care and the ability to review complete, real-time results, clinicians can improve patient's adherence, flag risks and intervene before they become acute problems. Alternatively or additionally, in some embodiments the system includes a stimulation module in each of the one or more insoles and a manual activation interface for the stimulation module. Alternatively or additionally, in some embodiments the stimulation module includes at least one member of the group consisting of a physical stimulator, a laser, a vibrator and a source of electric current.

In some exemplary embodiments of the invention there is provided a system including: (a) a data processor designed and configured to receive one or more output signal(s) from sensors in insoles and translate the output signal(s) to user advice; and (b) a user interface presenting the user advice.

In some embodiments, the data processor resides in a device selected from the group consisting of a smartphone, smartwatch, a PC (personal computer) and a tablet. Alternatively or additionally, in some embodiments the system includes a wireless communication link between the sensors and the data processor. Alternatively or additionally, in some embodiments the user advice includes a set of instructions for manual adjustment of individual height adjustment mechanisms in an insole. Alternatively, or additionally, in some embodiments the user advice includes an alert concerning a nascent foot ulcer. Alternatively or additionally, in some embodiments the clinical data collected is used to measure patient adherence and to enable remote continues monitoring. With this continuity of monitoring and the ability to review complete, real-time results, clinicians can improve patient's adherence, flag risks and intervene before they become acute problems.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature. The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase "adapted to" as used in this specification and the accompanying claims imposes additional structural limitations on a previously recited component. The term "method" refers to manners, means, techniques and procedures for accomplishing a given task including, but not limited to, those manners, means, techniques and procedures either known to, or readily developed from known manners, means, techniques and procedures by practitioners of architecture and/or computer science. Implementation of the method and system according to embodiments of the invention involves performing or completing selected tasks or steps manually, automatically, or a combination thereof. Moreover, according to actual instrumentation and equipment of exemplary embodiments of methods, apparatus and systems of the invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIG. 10A is a transverse cross section of an exemplary height adjustment mechanism using a screw according to some exemplary embodiments of the invention;

FIG. 10B is a side view of a portion of the exemplary height adjustment mechanism of FIG. 10A;

FIG. 10C is a bottom view of a portion of the exemplary height adjustment mechanism of FIG. 10A showing a manual adjustment interface;

FIG. 10D is a side view of an exemplary diagonal joint rotary lift height adjustment mechanism according to some exemplary embodiments of the invention in a closed (retracted) operational state with an inset depicting an upper portion of the mechanism disengaged from the lower portion in a bottom perspective view;

FIG. 10E is a side of the height adjustment mechanism of FIG. 10D in an open (extended) operational state;

FIG. 10F is a side view of an exemplary bayonet mount height adjustment mechanism according to some exemplary embodiments of the invention;

FIG. 10G is a side view of the bayonet mount height adjustment mechanism of FIG. 10F rotated 90° with respect to FIG. 10F;

FIG. 10H is a bottom view of a portion of the exemplary height adjustment mechanism of FIGS. 10F and 10G showing a manual adjustment interface;

DETAILED DESCRIPTION OF EMBODIMENTS

Embodiments of the invention relate to adjustable insoles and systems that include them or communicate with them. Specifically, some embodiments of the invention can be used to adjust insoles various static and/or dynamic conditions of different users and/or to adjust insoles to different activities of a same user. Alternatively, or additionally, some embodiments of the invention detect and/or diagnose and/or warn a user of a nascent foot ulcer and/or other foot disorders and/or to initiate and enable correction and/or adjustment and/or treatment plans. According to various exemplary embodiments of the invention the treatment plans are implemented manually and/or automatically.

The principles and operation of insoles and/or systems according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and is not limiting.

Overview

Many exemplary embodiments of the invention employ an insole. An exemplary insole is described here to avoid repetition of details when explaining specific embodiments of the invention hereinbelow.

Figure 1A:
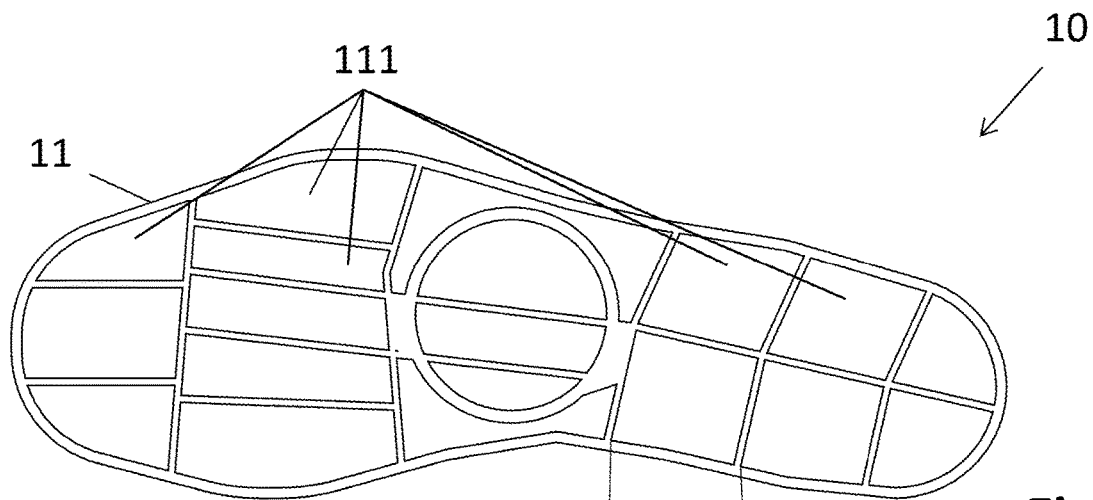
FIG. 1A is a schematic representation of a sensor layer of an insole, according to an exemplary embodiment of the invention.
Figure 1B:
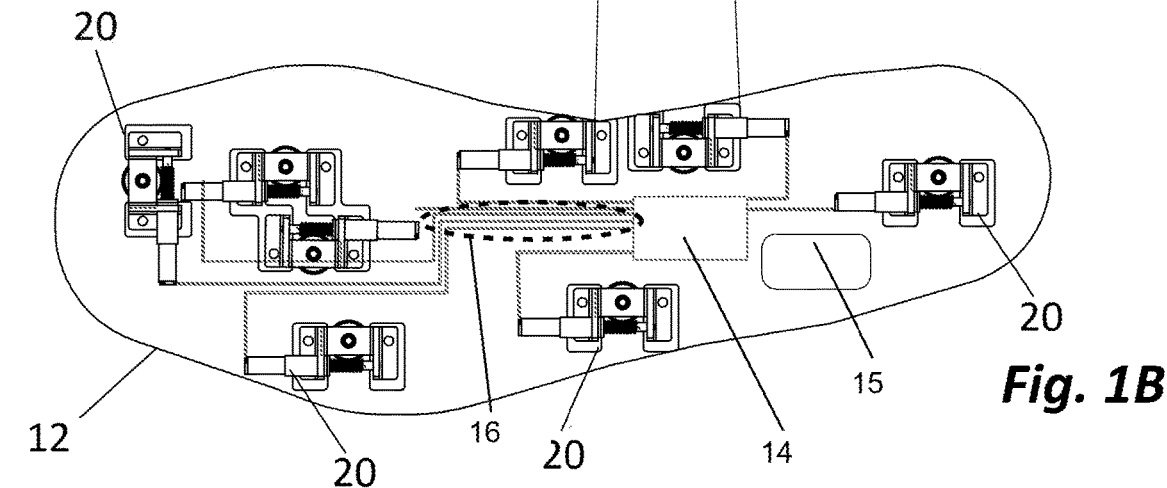
FIG. 1B is a schematic representation of an electronics layer of an insole, according to an exemplary embodiment of the invention.

FIG. 1A and FIG. 1B show an insole, indicated generally as 10, amenable to use in many embodiments of the invention. Depicted exemplary insole 10 includes 2 layers. In the depicted embodiment, the layers are sensor layer 11 (FIG. 1A), electronics/adjustment layer 12 (FIG. 1B).

In the depicted embodiment, insole 10 includes a diagnostic layer 11 (FIG. 1A) upon which a plurality of sensors 111 are deployed. In some embodiments layer 11 is flexible. In some embodiments sensors 111 include pressure sensors and/or temperature sensors and/or shear forces sensors and/or humidity sensors. In some embodiments diagnostic layer 11 is composed of a polyester film with mechanical properties, a highly conductive textile and a nano-scale sensing material. In some exemplary embodiments of the invention, layer 12 includes a stimulation source (e.g. vibrator). In some embodiments, the vibrator is incorporated in data processor 14.

In some embodiments diagnostic layer 11 includes a flexible film adhered to a conductive layer which conveys output from sensors 111 to an electronic circuitry layer 12 (FIG. 1B).

In some embodiments diagnostic layer 11 and electronic circuitry layer 12 are bonded by a double-sided adhesive. When a foot applies pressure to layer 11, layers 11 and 12 form an electrical contact and are switched on into a sensing mode. In the sensing mode the output resistance of the sensing area changes with pressure.

For the purposes of example alone, electronic circuitry layer 12 includes contact pads and/or a wireless communication module (e.g., Bluetooth or infrared) and/or one or more batteries 15 and/or a wireless charging component and/or internal memory storage and/or wireless syncing connection and/or microcontroller and/or a data processor 14 and/or printed circuit boards and/or USB connectors and/or a charging port and/or connecting wires 16 and/or an accelerometer and/or gyroscope. In some exemplary embodiments of the invention, one or more of these components are provided as part of a printed circuit board or microcontroller Adjustment/electronics layer 12 (FIG. 1B) includes a plurality of adjustment mechanisms 20 adapted to alter topography of a top surface (in contact with the user's plantar) of insole 10. In some embodiments, adjustment mechanisms 20 move in a coordinated manner, as will be explained in greater detail hereinbelow. Alternatively or additionally, in some embodiments mechanisms 20 are covered by pads.

According to various exemplary embodiments of the invention adjustment mechanisms 20 include pistons and/or piezoelectric materials and/or motors (e.g. step motors), gears (e.g. bevel gears, worm-drive gears, etc.) and/or spring-loaded mechanisms and/or hydraulic actuators. In some embodiments adjustment/electronics layer 12 includes any number of these mechanisms in combination.

For the purposes of example alone, cushioning and supporting materials on all insole layers can include: memory foam, foam, silicone, a butyl rubber, neoprene, polyurethane, EVA, sponge, gel, leather, polymers and synthetic materials.

Figure 2:
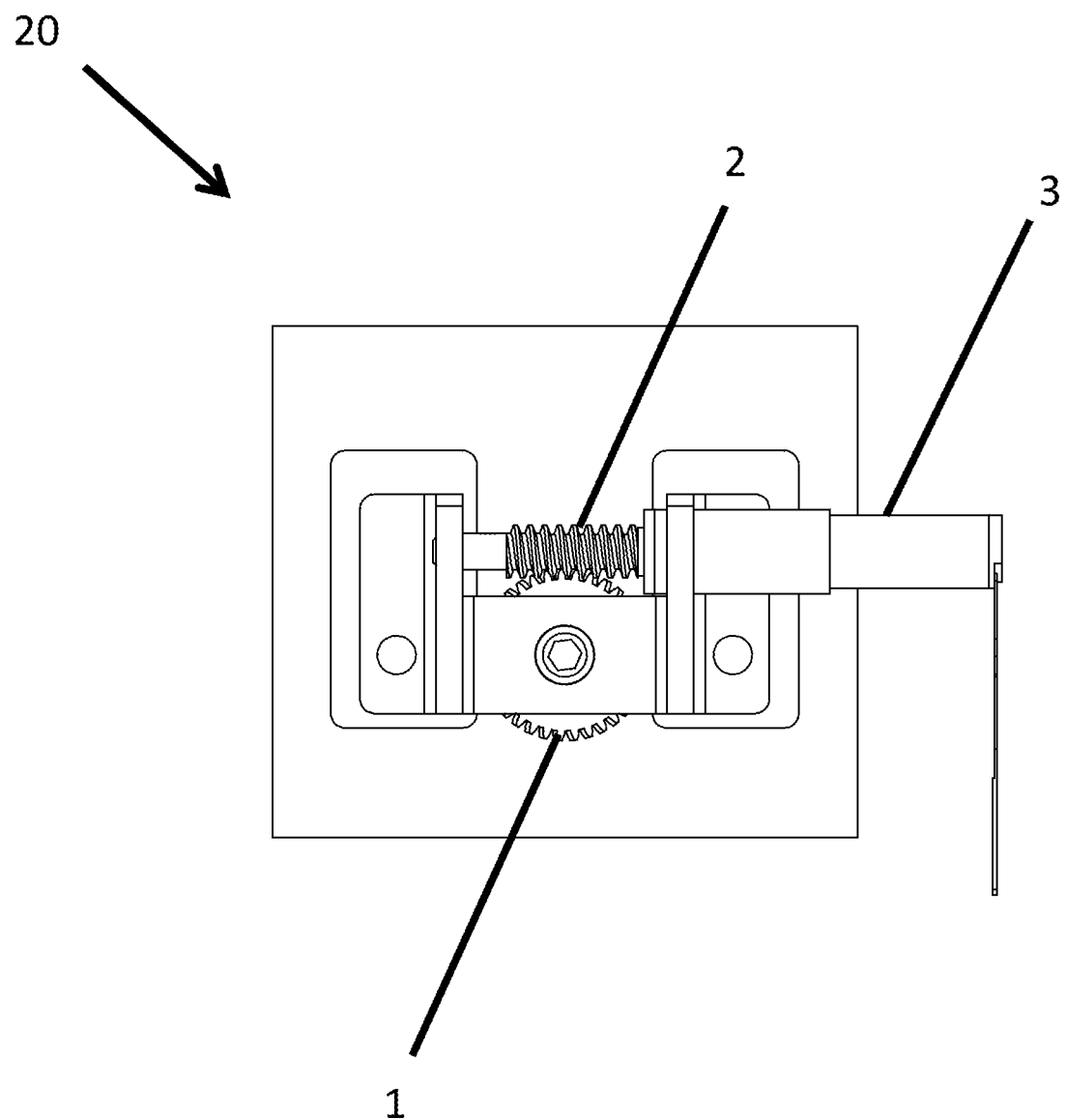
FIG. 2 is a schematic representation depicting a worm-drive gear piston suitable for use as a part of an insole adjustment mechanism, according to an exemplary embodiment of the invention.

FIG. 2 is a schematic top view of a worm-drive gear piston, indicated generally as 20, with worm-wheel 1, worm 2 and worm-shaft 3. According to some embodiments of the invention, adjustment/electronics layer 12 comprises a plurality of worm-drive gear pistons 20 deployed therein as schematically indicated in FIG. 1B. For example, each individual worm-drive gear piston 20 is configured to move a corresponding cover pad to a specific level, resulting in a controlled deformation of insole 10. In some exemplary embodiments of the invention, the depicted mechanism has a thickness of 4 mm or less when oriented in the insole. The insole itself may have a thickness of 5 to 50 mm.

Figure 3A:
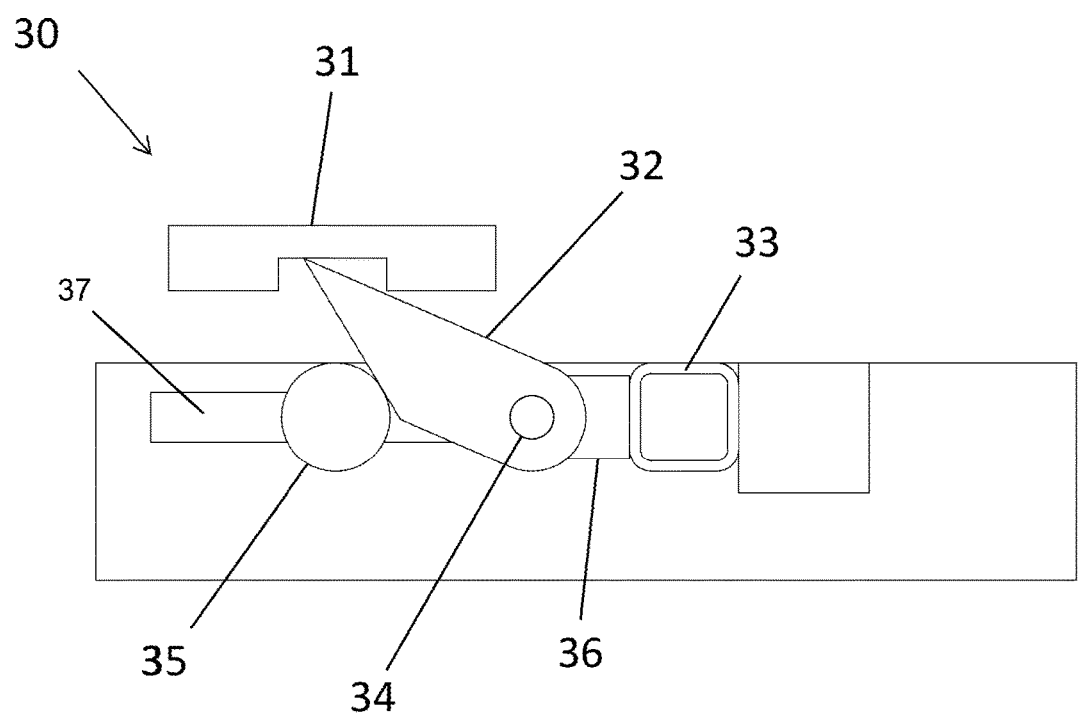
FIG. 3A is a schematic cross-sectional view of a cylinder-based lift system that pushes and/or pulls a lifting blade suitable for use as a part of an insole adjustment mechanism, according to an embodiment of the invention.

FIG. 3A is a schematic cross-sectional view of another adjustment mechanism indicated generally as 30, suitable for use in the context of adjustment/electronics layer 12 of FIG. 1B. In the depicted embodiment, adjustment mechanism 30 includes a displaceable blade 32, a pad 31, and motor assembly 33 and coupling 36 configured to cause blade 32 to pivotally move with respect to axis 34. In some embodiments, pivotal movement of blade 32 changes the level of pad 31. In the depicted embodiment motor assembly 33 turns the screw 37 and pulls or pushes lifting member 35 to apply force on a bottom surface blade 32 through lifting member 35 causing pivotal displacement of blade 32 with respect to pivot axis 34 raising pad 31. The coupling 36 connects the screw 37 to the motor 33 and transfers the movement of motor 33 to screw 37 and causes a change in position of lifting member 35 to raise/lower blade 32.

Figure 3B:
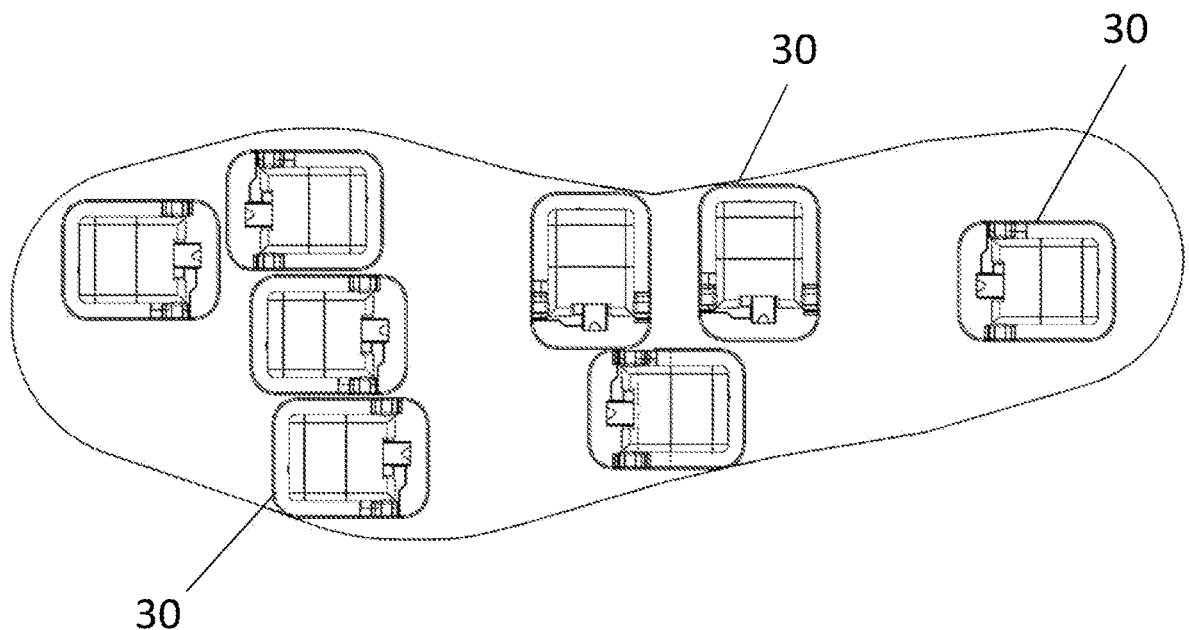
FIG. 3B is a schematic top view of an insole provided with a plurality of the insole adjustment mechanisms of FIG. 3A, according to an exemplary embodiment of the invention.

FIG. 3B is a top view of an exemplary insole layer schematically illustrating arrangement of a plurality of the adjustment mechanisms 30 of FIG. 3A, according to an embodiment of the invention. In some embodiments, adjustment mechanisms 30 of FIG. 3A replace mechanisms 20 in FIG. 1B.

Figure 3C:
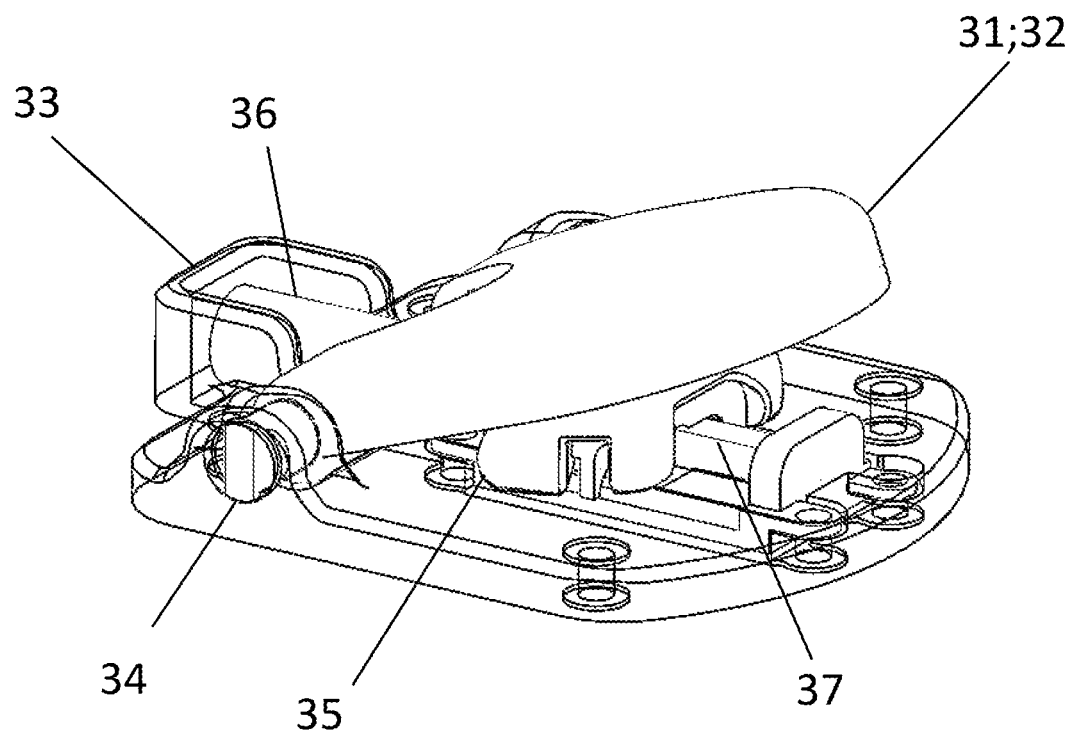
FIG. 3C is a perspective view of an adjustment mechanisms of FIG. 3A, according to an exemplary embodiment of the invention in an open position.
Figure 3D:
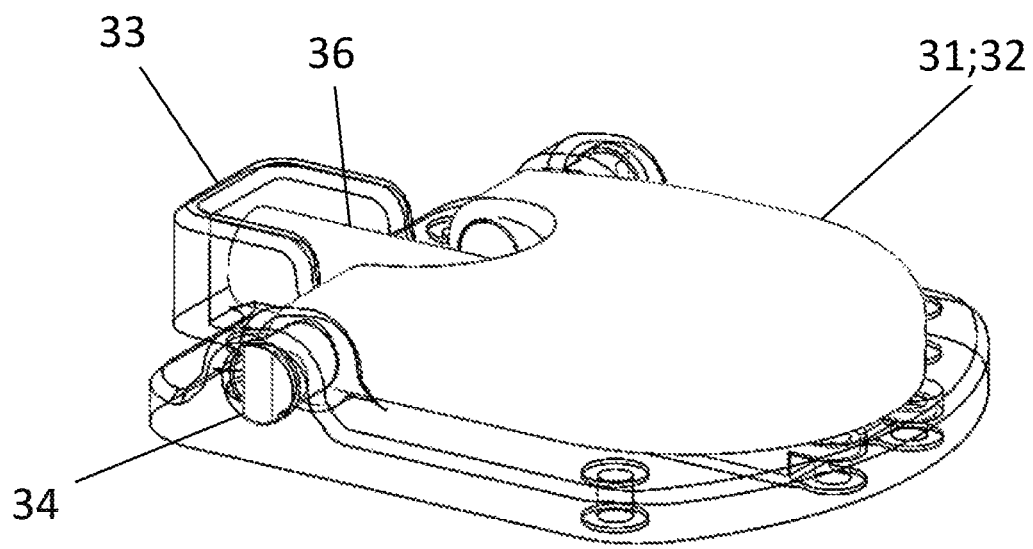
FIG. 3D is a perspective view of the adjustment mechanism of FIG. 3C in a closed position.

FIG. 3C is a perspective view of the adjusting mechanism in FIG. 3A depicting the pad 31 raised by the rotation of screw 37 when lifting member 35 is retracted. FIG. 3D is a three-dimensional illustration is a perspective view of the adjusting mechanism in FIG. 3C, in a closed position.

Exemplary Application Scenarios

Figure 4:
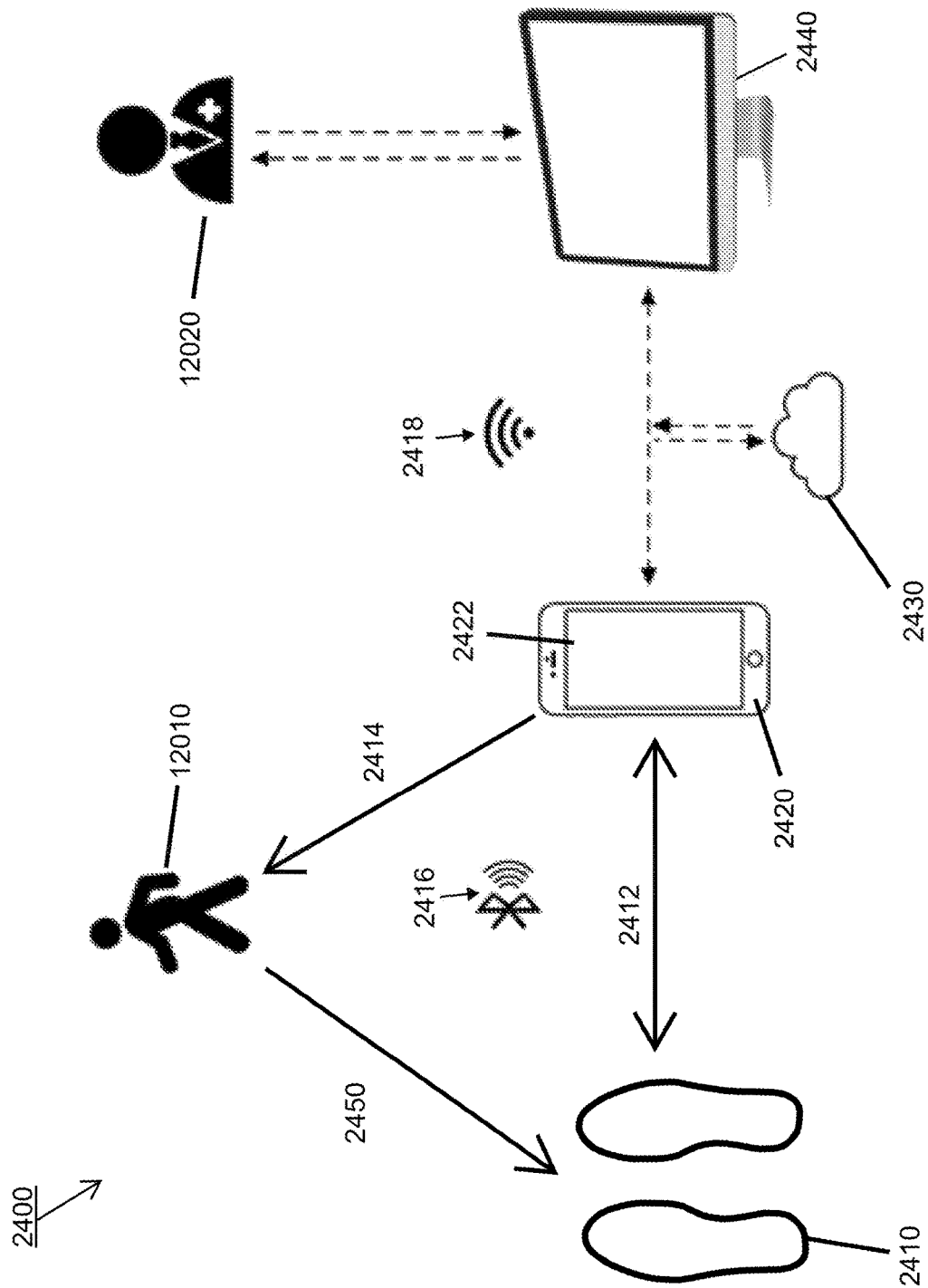
FIG. 4 is a schematic system diagram illustrating data flow according to various exemplary embodiments of the invention.

FIG. 4 is a schematic representation of a system, indicated generally as 2400. According to various exemplary embodiments of the invention system 2400 either provides instructions for manual adjustment of individual height adjustment mechanisms in an insole, or sends digital signals to the height adjustment mechanisms so that the adjustment is performed automatically in response to the signals.

In the depicted embodiment, insole device 2410 and the analysis and evaluation tool 2420 are synced via Bluetooth 2416 and each primarily controlled by user 12010. In various embodiments transmitting and receiving of data occurs continuously or periodically. In the case of periodic transmission/receiving data is stored in a computer memory in device 2410 and/or 2420 and/or 2440 and/or in cloud storage 2430. In the depicted embodiment, data is compiled and displayed, either continuously, or in the form of summaries or regular reports to user 12010 and/or healthcare professional 12020 by display 2422 of device 2420 and 2440 respectively. In some embodiments, healthcare professional 12020 is alerted online through dashboard platform 2440 when 12010 is flagged as being at risk. Alternatively or additionally, in some embodiments healthcare professional 12020 reviews real time results, monitors and treat patient(s) 12010, remotely, by modifications to 2410 through a treatment regimen via tool 2440 and/or 2420. Alternatively, or additionally, in some embodiments, data is stored on a cloud server 2430 with AI and/or big data and/or machine learning capabilities. In some embodiments server 2430 uses comparative scientific and/or personal historic data to build personalized models and/or make predictions and/or provide feedback and/or provide treatment suggestions and/or pressure off-loading correction plans and/or serve as early warning indicators of injury and/or ask for personal input information. Alternatively, or additionally, in some embodiments, medical advice 2414 is generated autonomously by an algorithm command from digital processor 2420 and/or cloud-based 2430 AI and/or ML and/or data science algorithm.

Depicted exemplary embodiment 2400 includes one or more insoles 2410 with a plurality of height adjustment mechanisms integrated across at least a portion of an area thereof.

In some embodiments there is an automated adjustment interface and a treatment pan is relayed 2412 from device 2420 to height adjustment mechanisms in insoles 2410.

In other exemplary embodiments of the invention, there is manual adjustment interface for each of the height adjustment mechanisms. Exemplary height adjustment mechanism types and manual adjustment interfaces are described hereinbelow. In addition, insoles 2410 include one or more sensors providing one or more output signal(s) 2412.

In the depicted embodiment, system 2400 includes a data processor 2420 (depicted here as a smartphone) designed and configured to translate output signal(s) 2412 to alerts and/or user advice 2414 and a user interface 2422 (depicted here as the screen of the smartphone) presenting user advice 2414 and/or analyzed data. In some embodiments User advice 2414 results from a diagnosis process that wirelessly connects 2418 to cloud network 2430 to compare scientific data and/or save data and/or run AI, ML algorithms. User 12010 receives alert and/or user advice 2414 from interface 2422 and performs manual adjustment 2450 of each of the plurality of height adjustment mechanisms in accord with advice 2414. In some embodiments health specialist 12020 monitors real-time results and/or alerts and/or treats and/or manages patient's feet health, remotely, reducing need of clinic visits from interface 2440 and can intervene via medical correction plan 2414 if needed.

In the depicted embodiment, data processor 2420 resides in a device external to said insoles. According to various exemplary embodiments of the invention the device external to insole 2410 is a smartphone as depicted, a PC (personal computer), a smartwatch or a tablet. Alternatively, or additionally, in some embodiments the system includes a wireless communication link (e.g., Bluetooth 2416) between the insole 2410 and data processor 2420.

In other exemplary embodiments of the invention, data processor 2420 resides in insoles 2410. According to these embodiments, user advice 2414 is transmitted from insoles 2410 and presented to user 12010 via interface 2422.

In some exemplary embodiments of the invention, user advice 2414 includes a set of instructions for manual adjustment of each of the height adjustment mechanisms.

In some embodiments the sensors are always gathering data and completing a user's gait analysis and/or pressure distribution map and/or temperature map which transferred to user interface (patient and/or health specialist). Using different algorithms and ML, current information can be cross-referenced and various pathological patterns identified over time and therefore to engage an action.

In some embodiments a health professional can adjust each height adjustment mechanism manually according to his knowledge and physical examination. A health professional or user can decide according to the diagnosis (e.g. pressure map) showed in the user interface where to adjust by seeing the high pressure and/or temperature areas on map and intuitively act by the software recommendation (e.g. "High pressure detected in medial left arch. Change x1y1, x2y2 high adjustment mechanisms in +2 mm) or remotely, done by user but guided by the health specialist. The health professional can also send a clinic invite directly to the patient for a further observation and/or treatment and/or adjustment. According to these embodiments user 12010 manually implements 2450 the treatment recommendations via the height adjustment recommendations via the height adjustment mechanisms in insoles 2410.

Alternatively, or additionally, in some embodiments user advice 2414 includes an alert concerning a nascent foot ulcer. In some embodiments the alert includes offloading adjustments instructions when aberrant pressures were detected and/or foot temperature and/or correcting user's gait and/or orthopedic disorder.

In some embodiments, system 2400 includes a stimulation module (e.g. 539 in FIG. 5B) in each of insoles 2410 and a manual and/or automate activation interface for the stimulation module. In some embodiments, the manual activation interface is provided on screen 2422 of phone 2420. According to various exemplary embodiments of the invention the stimulation module includes at least one member of the group consisting of a physical stimulator, a laser, a vibrator and a source of electric current.

Figure 5A:
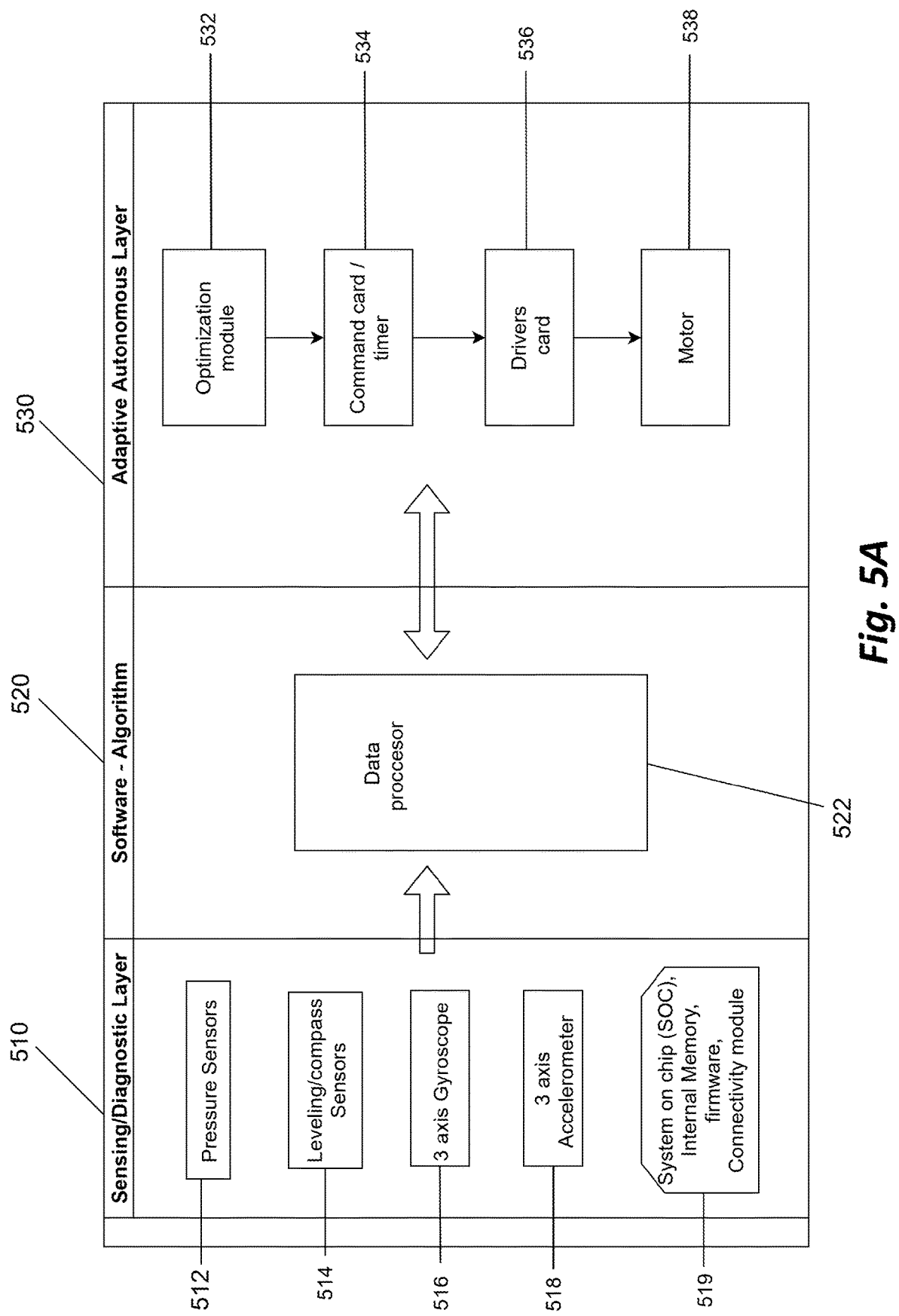
FIG. 5A is a diagram illustrating layers in a system according to an exemplary embodiment of the invention.

FIG. 5A is a more detailed representation of the flow of information showing a smart diagnostic layer 510 including pressure sensors array 512, and/or levelling sensors 514 and/or, gyroscopes 516 and/or, accelerometers 518, and/or internal memory firmware and a connectivity module 519. In some exemplary embodiments of the invention, accelerometers 518 and/or gyroscopes 516 are inertial sensors, and measure the movement of the subject such as acceleration and angular velocity. In some exemplary embodiments of the invention, gyroscopes 516 and/or accelerometers 518 are 3 axis sensors. In some embodiments a levelling sensor 514 (compass) provides a baseline when the inertial sensors (accelerometer and gyroscope) are calibrated. Alternatively or additionally, in some embodiments, pressure sensor array 512 provides a high-resolution pressure map of the sole of the foot.

The data from diagnostic layer 510 is fed to a software algorithm layer 520 including one or more data processors 522. In some embodiments algorithm layer 520 provides a gait characterization analysis. In some embodiments processor(s) 522 unit have artificial intelligence capability and/or big data analysis capability and/or machine learning capability. Data processor 522 provides an output signal to adaptive autonomous layer 530 which includes an optimization module 532, a command card 534, a driver card 536 and motors 538 which operate the adjustment mechanisms in the insoles as described above.

Figure 5B:
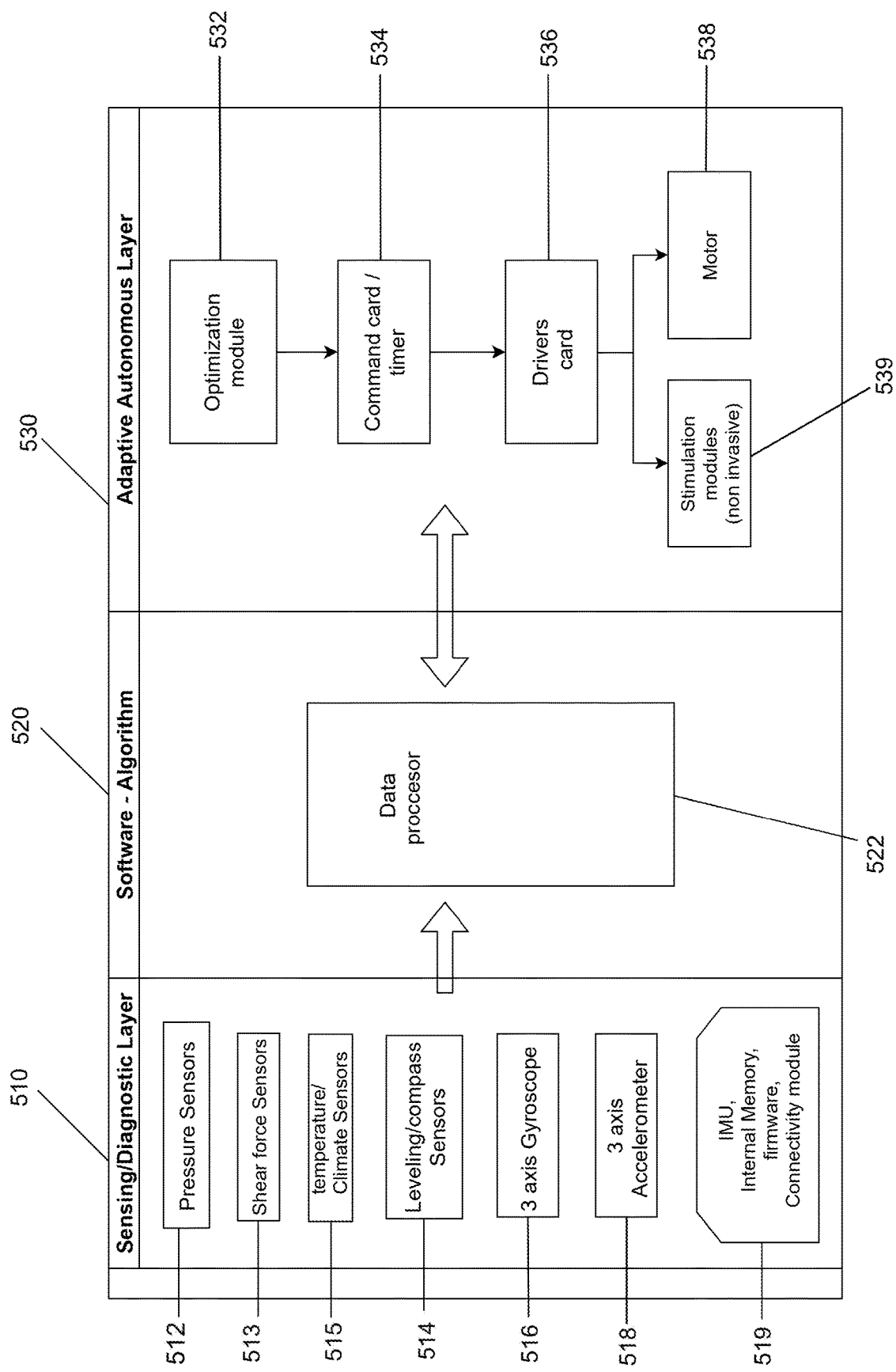
FIG. 5B is a diagram illustrating layers in a system according to another exemplary embodiment of the invention.

FIG. 5B is another detailed representation of the flow of information for an exemplary embodiment adapted to detect and/or treat diabetic foot and/or neuro-orthopedic mobility disorders (e.g. Parkinson). In the depicted embodiment, diagnostic layer 510 also includes shear force sensors 513 and/or temperature sensors and/or climate control sensors 515. The objective of foot temperature monitoring and/or pressure and/or shear forces in shoes is to identify impending inflammatory foot conditions, such as DFUs, infection, and acute Charcot neuroarthropathy episodes. Data from diagnostic layer 510 is collected and fed to a software algorithm layer 520 for processing in one or more data processors 522. In some embodiments data processor(s) 522 have artificial intelligence capability and/or big data analysis capability and/or machine learning capability. Data processor 522 provides an output signal to adaptive autonomous layer 530 which includes an optimization module 532, a command card 534, a driver card 536 and motors 538 which operate the adjustment mechanisms in the insoles as described above.

In some embodiments the adaptive layer 530 include active, non-invasive, stimulation micromechanical module 539 to user's external plantar surface. In some embodiments non-invasive stimulation is part of the treatment plan and/or contributes to early prevention of DFUs to reduce targeted symptom and/or to improve mobility in quality and functional capacity for outpatients in real world rehabilitation. In some embodiments of the invention, module 539 includes one or more haptic vibration motors and/or actuators, vibrators and/or wireless functional electrical stimulator(s).

The benefits of stimulation for plantar fasciitis and/or flexor muscles to reduce gait and balance impairment and/or improve plantar sensation in neuropathic patients are already known.

Figure 6:
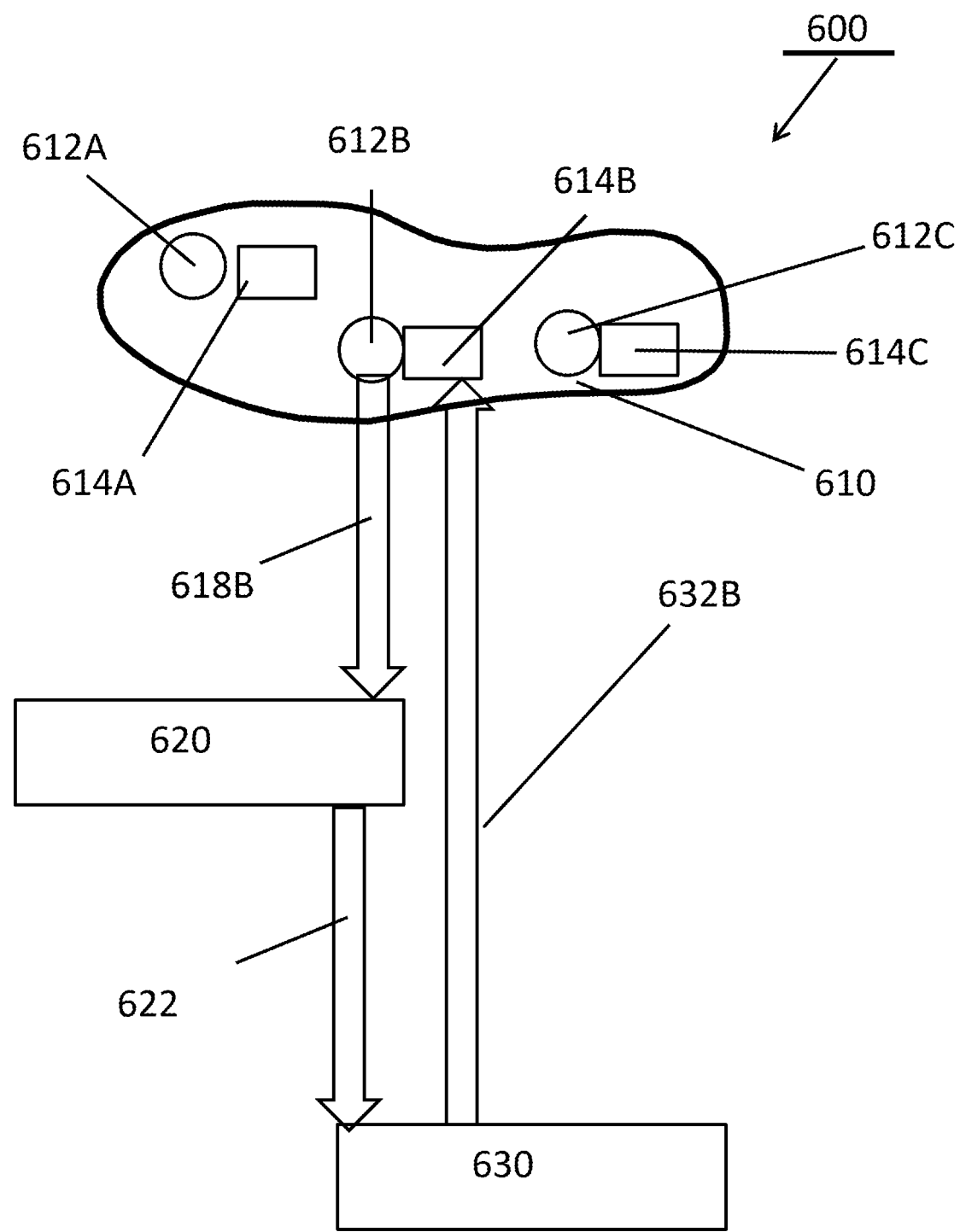
FIG. 6 is a simplified schematic representation of a system according to some embodiments of the invention.

Exemplary sensor responsive system FIG. 6 is a simplified schematic representation of a responsive insole system, indicated generally as 600, according to some embodiments of the invention. In the depicted embodiment, system 600 includes an insole 610 with a plurality of sensors 612 (612A, 612B and 612C are depicted for clarity although a much larger number is typically provided in actual use) and a plurality of adjustment mechanisms 614 (614A, 61413 and 614C are depicted for clarity although a much larger number is typically provided in actual use) deployed thereupon. Each of sensors 612A, 612B and 612C provides a data output signal 618 (in the figure only 6186 is depicted for clarity).

Depicted exemplary system 600 also includes a data processor 620 designed and configured to receive data output signals (e.g. 61813 as depicted) from sensors 612 (e.g. 612A, 612B and 612C as depicted) and analyze data from the output signals. Based upon this analysis, data processor 620 provides a response plan 622 as an output.

In the depicted embodiment, system 600 includes an implementation module 630 which receives response plan 622 and translates it to a plurality of response signals 632 (only 632B is depicted for clarity), and transmits each response signal of the plurality of response signals to a specific one of the plurality of adjustment mechanisms. Each of the adjustment mechanisms responds adjusting its height in accord with the response signal it receives.

Specifically, in the depicted embodiment sensor 6126 provides output 6186 which gives rise to response signal 6326 which operates adjustment mechanism 61413. Concurrently (although not depicted) sensor 612A provides output 618A which gives rise to response signal 632A which operates adjustment mechanism 614A. Concurrently (although not depicted) sensor 612C provides output 618C which gives rise to response signal 632C which operates adjustment mechanism 614C.

Because data processor 620 analyzes output signals 618 as a group, response plan 622 is a coordinated response plan based upon sensors in different areas of the insole. As a result, each of response signals 632 is influenced by data collected by all of the sensors.

According to various exemplary embodiments of the invention sensors 612A; 6126 and 612C are each independently selected from the group consisting of pressure sensors, temperature sensors, levelling sensors, gyroscopes and accelerometers.

According to various exemplary embodiments of the invention data processor 620 is located in or on insole 610 and/or is worn or carried by a user of the insole (e.g. in a smartphone, smartwatch or dedicated wearable device) and/or at a remote server.

According to various exemplary embodiments of the invention each of adjustment mechanisms 614A, 61413 and 614C is independently selected from the group consisting of pistons, piezoelectric materials, motors, gears, bevel gears, worm-drive gears, spring loaded mechanisms and hydraulic actuators.

In some exemplary embodiments of the invention, system 600 includes a stimulation module (not depicted in FIG. 6; see 539 in FIG. 5B) under control of implementation module 630. According to these embodiments, response plan 622 includes a stimulation signal 632. According to various exemplary embodiments of the invention the stimulation module includes at least one member of the group consisting of a physical stimulator, a laser, a vibrator and a source of electric current.

Exemplary Multi User System

Figure 7:
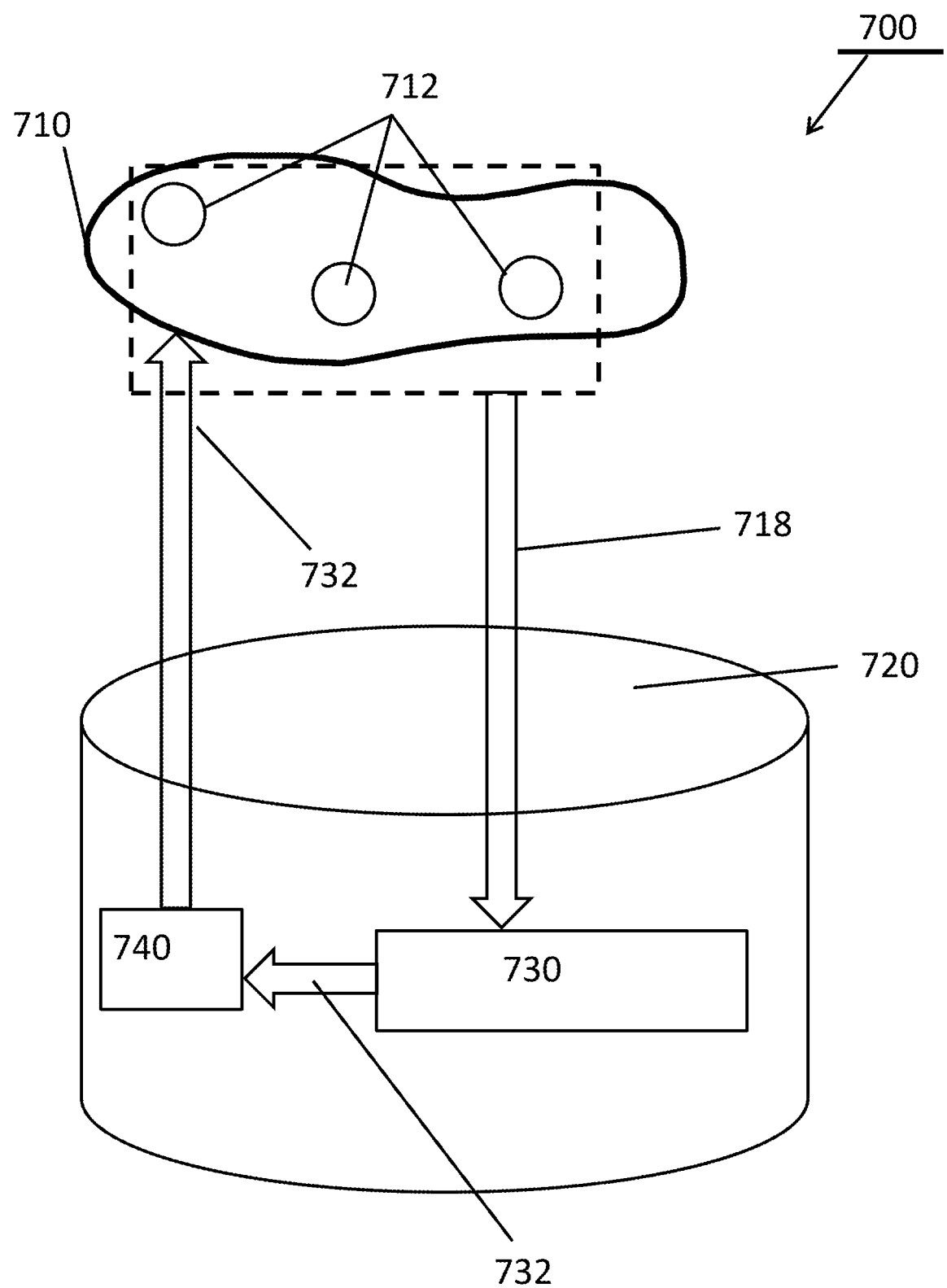
FIG. 7 is a simplified schematic representation of a system according to some embodiments of the invention.

FIG. 7 is a simplified schematic representation of a multi user system, indicated generally as 700 according to some embodiments of the invention. In the depicted embodiment, system 700 includes a plurality of insoles 710 (only one is depicted for clarity) equipped with sensors 712 producing time stamped data output signals 718 labeled with UIDs (unique identifiers) for users of specific insole. In some embodiments a single data output signal reflects data from a large number of sensors 712 distributed across insole 710. In some embodiments each sensor has a sensor ID indicating its position on insole 710 and this positional information is preserved in output signal 718.

In the depicted embodiment, time stamped output signals 718 are received and stored in a database labeled with their UIDs. In some embodiments database 720 contains digital medical records (DMR) of patients associated with the UIDs or communicates with other databases that contain the DMR to retrieve data relevant to foot or gait related issues of specific subjects in different scenarios.

Alternatively, or additionally, in some embodiments system 700 includes one or more data processors 730 receiving data output signals 718 from sensors 712. In some embodiments processor(s) 730 analyze data from output signals 718 correlated with a specific UID and output a UID specific response plan 732 which is time stamped and stored. Alternatively, or additionally, in some embodiments, processors 730 relay response plan 732 to a response plan delivery module 740 which transmits UID specific response plan 732 to insoles associated with the UID.

Alternatively, or additionally, in some embodiments analysis of changes in sensor output 718 over time in conjunction with intervening response plan(s) 732 permits evaluation of treatment efficacy of the response plan. Alternatively, or additionally, in some embodiments response strategy 732 is prepared based upon a DMR stored in database 720.

Although system 700 is presented simplistically here, implementation of the system with a large number of users with a variety of different medical conditions contributes to a large amount of sensor data 718 in database 720 before and after implementation of response plan(s) 732. In some embodiments implementation of a machine learning algorithm on database 720 contribute to an improvement in efficacy of future response plans.

Exemplary User Input Driven System

Figure 8:
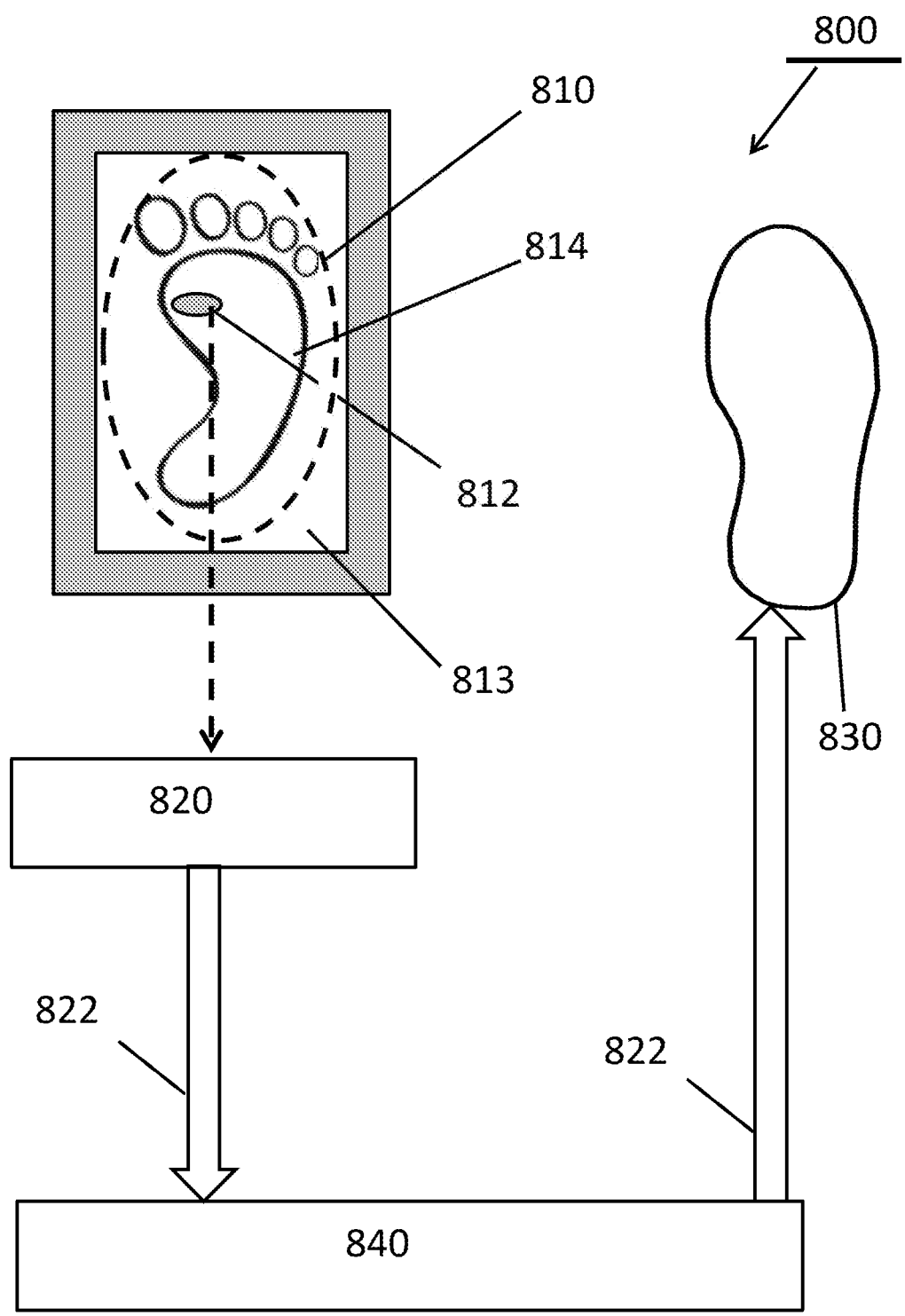
FIG. 8 is a simplified schematic representation of a system according to some embodiments of the invention.

FIG. 8 is a simplified schematic representation of a user input driven system, indicated generally as 800, according to some embodiments of the invention. In the depicted embodiment, system 800 includes a user interface (UI) 810 adapted to receive user input defining a problem 812 area on the sole 814 of a foot and a data processor 820 including a translation module adapted to translate user input (problem area 812) into a response signal 822. In the depicted embodiment, UI 810 is provided via a touch screen 813. According to various exemplary embodiments of the invention touchscreen 813 is part of a smartphone or tablet or smartwatch. Alternatively, or additionally, in various embodiments UI 810 displays sole 814 as a diagram or as a photograph of the user's foot.

According to various exemplary embodiments of the invention data processor 820 resides at least one location selected from the group consisting of in an insole, in a device worn/carried by a user of an insole and at a remote server. According to various exemplary embodiments of the invention a device worn/carried by the user indicates a smartphone, a smartwatch, a tablet or a dedicated wearable device.

Alternatively, or additionally, in some embodiments system 800 includes an insole 830 comprising an adjustment mechanism (not depicted) adapted to respond to response signal 822 and a response signal delivery module 840 adapted to transmit response signal 822 to insole 830. According to various exemplary embodiments of the invention the adjustment mechanism includes at least one member of the group consisting of pistons, piezoelectric materials, motors, gears, bevel gears, worm-drive gears, spring loaded mechanisms, blades and hydraulic actuators. In other exemplary embodiments of the invention, an adjustment command is controlled by a health supervisor or foot caregiver and is triggered remotely with outpatients and provides real time monitoring in real life setting.

Placement and operation of the adjustment mechanism is as described hereinabove and/or hereinbelow.

In some exemplary embodiments of the invention, system 800 includes a stimulation module (not depicted here; see 539 in FIG. 5B) responsive to response signal 822. According to various exemplary embodiments of the invention the stimulation module includes at least one member of the group consisting of a physical stimulator, a laser, a vibrator and a source of electric current.

Exemplary Insole

Figure 9A:
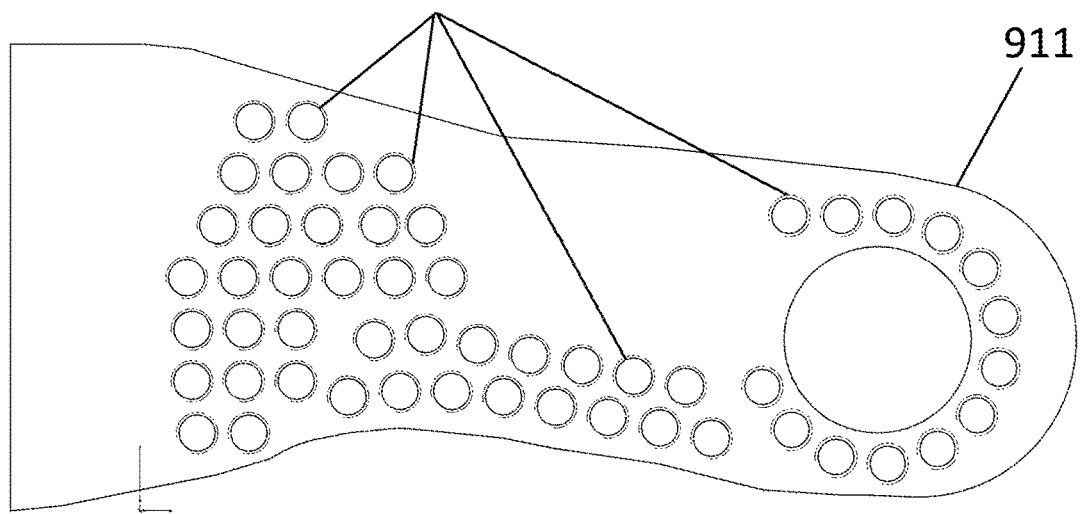
FIG. 9A is a diagrammatic representation of an arrangement of height adjustment mechanisms within an insole according to an exemplary embodiment of the invention.

FIG. 9A is a diagrammatic representation of an arrangement of height adjustment mechanisms 93 within an insole 911 according to an exemplary embodiment of the invention. In the depicted embodiment, height adjustment mechanisms are distributed under the heel, under the arch and under the ball of the foot.

Figure 9B:
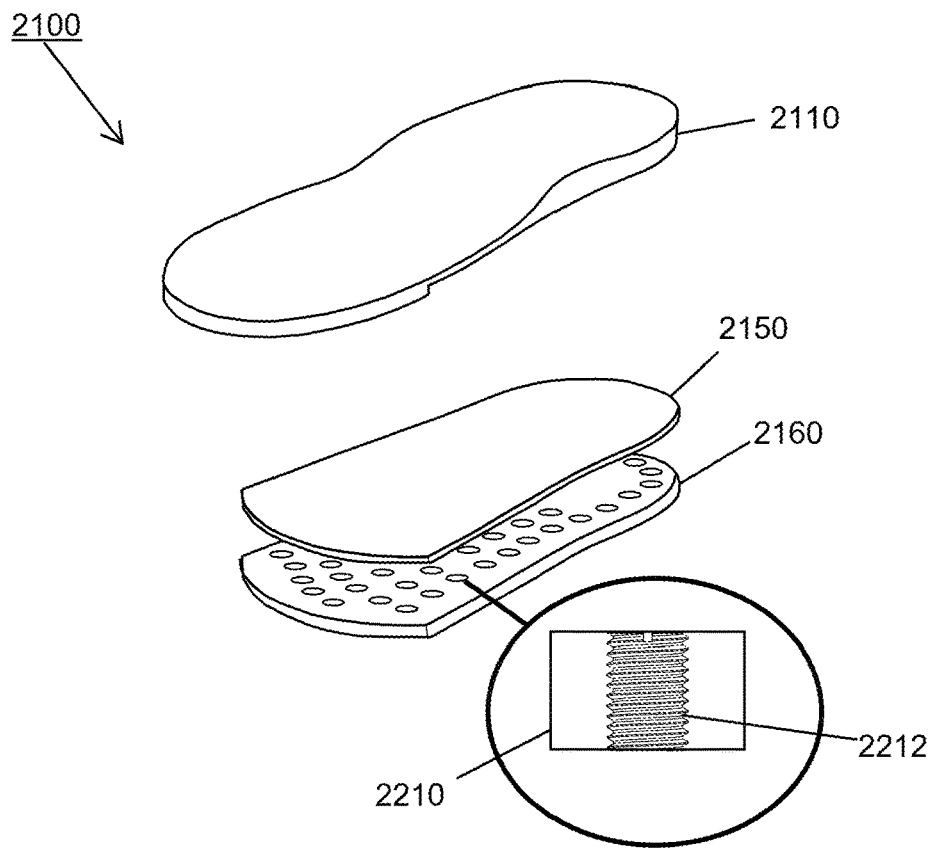
FIG. 9B is an exploded view of layers of an insole illustrating incorporation of height adjustment mechanisms according to an exemplary embodiment of the invention.

FIG. 9B is an exploded view, indicated generally as 2100, of layers of an insole illustrating incorporation of height adjustment mechanisms according to an exemplary embodiment of the invention. In FIG. 9B, 2160 is a base plate layer. In some embodiments layer 2160 is constructed of polypropylene. In the depicted embodiment, layer 2150 is a flexible cover layer. In some embodiments layer 2150 is made from a thin plastic material that insulates the adjustment mechanisms from the top layer and/or improves comfort. In the depicted embodiment, layer 2110 is an upper insole layer. According to various exemplary embodiments of the invention layer 2110 is made from foam and/or gel and/or Polyurethanes and/or other fabric. Each hole in layer 2160 is fitted with a height adjustment mechanism (shown in inset) described below in the context of FIG. 10A. In some embodiments each height adjustment mechanism includes a manual adjustment interface. According to various exemplary embodiments of the invention each height adjustment mechanism is independently selected from the group consisting of screws, a diagonal joint rotary lift, and a bayonet mount.

Figure 9C:
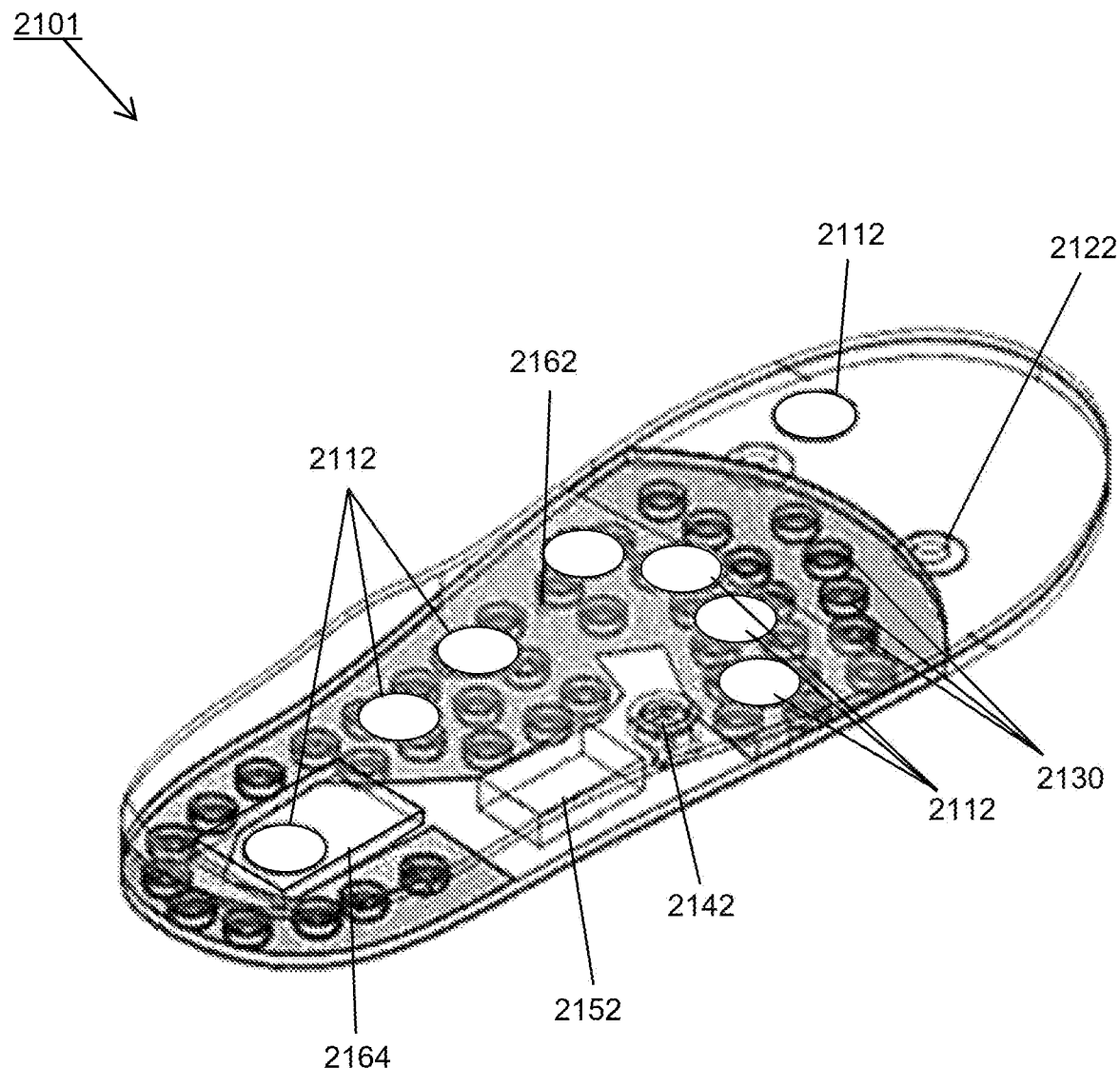
FIG. 9C is a top perspective view of an insole illustrating additional features according to an exemplary embodiment of the invention.

FIG. 9C is a top perspective view of an insole, indicated generally as 2101, illustrating additional features according to an exemplary embodiment of the invention. In this view, height adjustment mechanisms 2130 are visible. In the depicted embodiment, insole 2101 includes a magnetic connector 2142 and battery 2152. According to this embodiment battery 2152 powers the monitoring, analysis and connectivity capabilities and connector 2142 facilitates connection to an external power source for charging. Magnetic connector 2142 contributes to convenience of charging without taking insole 2101 out of the shoe. In some embodiments using a magnetic charging cable(s) (not depicted) it is possible charge both insoles with dedicated cable. Alternatively or additionally, magnetic connector 2142 can be moisture and/or waterproof. In other exemplary embodiments of the invention, employ wireless charging (e.g. with a dedicated charging mat upon which shoes containing the insoles are placed). In other exemplary embodiments of the invention, a kinetic energy charging system is embedded in the insole.

According to various exemplary embodiments of the invention battery 2152 provides power to sensors (e.g. 2112 and/or 2162) and/or micro-processors 2164 and/or IMUs and/or SOCs and/or board memory and/or connectivity modules and/or stimulation hardware (e.g., vibration motor and/or haptic engine and/or mini piezoelectric actuators). In some embodiments insole 2101 records data in an "offline mode" for a few hours or other period of time without connectivity to smart device. According to these embodiments battery 2152 provide power to operate monitoring, diagnostic and vibration capabilities. In the depicted embodiment, vibration motor 2122 applies low-level vibration. According to various exemplary embodiments of the invention low level vibration contributes to improvement in nerve function.

Improvement in nerve function has the potential to contribute to wellness and/or performance for many different types of wearers. For example, low-level vibration is potentially beneficial for stroke- or diabetes-related nerve damage and/or to improve balance and/or improve gait. Alternatively, or additionally, low level vibration might prevent injuries and/or falls and/or might help to assess nerve damage and/or decrease of plantar sensation. In some exemplary embodiments of the invention, delivering imperceptible mechanical vibrations to the feet, enhancing nerve sensory performance—which in turn improves one's balance, gait control, and sense of the spatial position and movement of different parts of the body. In some embodiments Operation of vibration motor 2122 is via a signal transmitted from a smartphone or 3rd party connected device or remote care management platform. In the depicted embodiment, pressure sensors 2112 are positioned in key points where ulceration and/or high pressure are most often observed. In the depicted embodiment, temperature sensor 2162 (1 is depicted for clarity but 3, 5, 7, 9 or intermediate or greater numbers are present in other embodiments) is positioned in one or more areas that statistically and medically are at high risk for ulceration and other pathologies.

FIG. 10A is a transverse cross section of an exemplary screw-based height adjustment mechanism according to some exemplary embodiments of the invention. In the depicted embodiment base 2210 contains a screw 2212 with a screwdriver slot 2214 (FIG. 10C). Screw 212, ascends or descends within base 210 in response to rotation of slot 2214. FIG. 10B is a side view screw 2212. FIG. 10C is a bottom view of screw 2212 showing a manual adjustment interface in the form of screwdriver slot 2214. Manual rotation of slot 2214 with a screwdriver causes screw 2212 to ascend or descend within an inner channel of base 2210.

FIG. 10D is a side view of an exemplary diagonal joint rotary lift height adjustment mechanism according to some exemplary embodiments of the invention in a closed (retracted) operational state with an inset depicting an upper portion of the mechanism disengaged from the lower portion in a bottom perspective view. According to the depicted embodiment, rotation of shaft 2224 causes a change in orientation of upper cover portion 2222 with respect to lower cover portion 2226 along contact surface 2225. As a result, top surface 2220 is raised as depicted in FIG. 10E. Rotation of shaft 2224 in the opposite direction lowers top surface 2220.

Referring now to the inset of FIG. 10D, extension (or retraction) of shaft 2224 is achieved by rotation of manual adjustment interface 2229 which is depicted here as a hexagonal socket that can be turned by an Allen wrench. Rotation of interface 2229 moves teeth 2227 on a bottom side 2221 of contact surface 2225 of upper portion 2222 with respect to corresponding teeth (not depicted) on a top side 2223 (FIG. 10E) of contact surface 2225 of lower portion 2226. Engagement of corresponding sets of teeth at 2221 and 2223 prevents rotation of 2222 with respect to 2226 in the absence of rotational force provided via manual adjustment interface 2229.

FIG. 10F is a side view of an exemplary bayonet mount height adjustment mechanism according to some exemplary embodiments of the invention. FIG. 10G is a side view of the bayonet mount height adjustment mechanism of FIG. 10F rotated 90° with respect to FIG. 10F.

FIG. 10H is a bottom view of a portion of the exemplary height adjustment mechanism of FIGS. 10F and 10G showing a manual adjustment interface, in the depicted embodiment insertion of a square rod in square hole 2236 allows rotation of shaft 2234 with respect to rectangular hole 2238.

In the depicted embodiment, shaft 2234 is fitted with rectangular protrusions 2232. When these protrusions are aligned with hole 2238 (as in FIG. 10G), shaft 2234 is free to ascend/descend through hole 2238. Rotation of shaft 2234 in either direction causes protrusions 2232 to be misaligned with hole 2238 and prevents shaft 2234 from ascending/descending through hole 2238. In this way rotation of square hole 2236 unlocks the mechanism every 90° and relocks it as soon as protrusions 2232 lose alignment with hole 2238.

Figure 11:
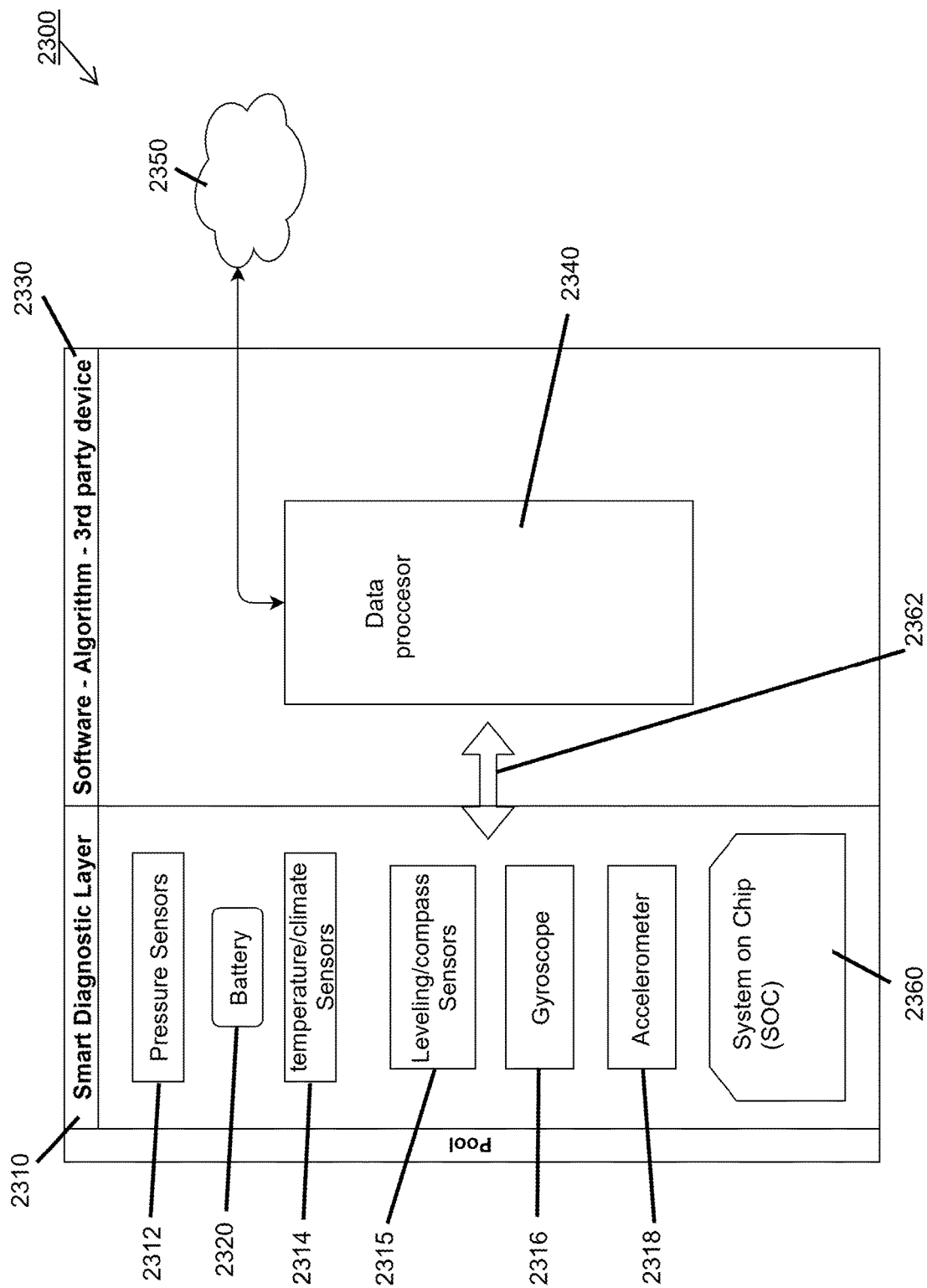
FIG. 11 is a schematic representation of a data acquisition layer of an insole according to some exemplary embodiments of the invention.

Alternatively, or additionally, in some embodiments insole 2100 includes one or more sensors. FIG. 11 is a schematic representation of a data acquisition layer, indicated generally as 2300, of an insole according to some exemplary embodiments of the invention. According to various exemplary embodiments of the invention the sensors include pressure sensors 2312 and/or sensors 2314 to obtain foot temperature microclimate temperature and humidity data of the foot in the insole of the footwear and/or a leveling-sensors 2315 and/or a gyroscope 2316 and/or an accelerometer 2318. The group of sensors of various types is indicated in FIG. 11 as smart diagnostic layer 2310. In the depicted embodiment, layer 2310 also includes a battery 2320 and system on chip (SOC) 2360. In some embodiments SOC 2360 includes integrated Wi-Fi and Bluetooth module. In the depicted embodiment, data acquisition layer 2300 includes a data communication channel 2362 configured to transmit an output signal from the one or more sensors to a data processor 2340. In the depicted embodiment, data processor 2340 is equipped with a software algorithm 2330 and/or is in communication with analytic software via network 2350. In some exemplary embodiments of the invention, the analytic software is cloud based. In some exemplary embodiments of the invention, data processor 2340 is physically present in insole 2100.

In some embodiments of the invention pressure sensors 2312 are woven in conductive fabric/textile as a one layer.

Single-layer pressure sensors have a high working performance and are thinner than multi-layer sensors.

Alternatively or additionally, in some embodiments insole 2100 includes a stimulation module (e.g. 539 in FIG. 5B) and a manual activation interface for the stimulation module. According to various exemplary embodiments of the invention the stimulation module includes at least one member of the group consisting of a physical stimulator, a laser, vibrator and a source of electric current.

Additional Exemplary System

Referring again to FIG. 4 system 2400 can also be described as a data processor 2420 designed and configured to receive one or more output signal(s) 2412 from sensors in insoles 2410 and translate said output signal(s) to user advice 2414 and a user interface 2422 presenting user advice 414.

System 2400 can perform continuous monitoring of foot plantar pressure and/or temperature and/or user's gait which is used to diagnose early foot ulceration forming and as result to dynamically output alerts and/or medical advice to user (offloading treating plan using the adjustments mechanisms) 2414 to user interface 2422 and/or to health specialist 12020 via user interface 2440. Consequently system 2400 can lead to reduction in diabetic foot ulcer recurrence.

According to various exemplary embodiments of the invention data processor 2420 resides in a device selected from the group consisting of a smartphone, smartwatch, a PC (personal computer) and a tablet. Alternatively, or additionally, in some embodiments the system includes a wireless communication link 2416 between the sensors and data processor 2420.

According to various exemplary embodiments of the invention user advice 2414 includes a set of instructions (e.g., as part of off-loading treatment plan) for manual adjustment of individual height adjustment mechanisms in an insole and/or user advice 2414 includes an alert concerning a nascent foot ulcer.

Exemplary Network Implementation

Referring again to FIG. 4, in some embodiments data processor 2420 evaluates output signal(s) 2412 with respect to comparative scientific data 2430 using an available network connection (e.g., Wi-Fi 2418) when formulating advice 2414. Alternatively, or additionally, in some embodiments data processor 2420 sends a query to one or more health specialists 12020 via a device 2440 belonging to that specialist using an available network connection (e.g., Wi-Fi 2418) when formulating advice 2414. Health specialist(s) 12020 can monitor and perform remote diagnosis and formulate care plan such to send a medical advice to user (e.g., adjustment recommendation) via interface 2440 that will appear to user 12010 through user interface 2422.

Exemplary Use Scenarios

The various embodiments of the invention described hereinabove will find utility in a wide variety of situations including orthopedic problems, neuro-orthopedic problems, diabetic heel, diabetic foot (ulcers, infection, Peripheral neuropathy), rehabilitation, Parkinson's disease, early diagnosis of Alzheimer's disease, Stroke, Obesity, Elderly falls, various musculoskeletal disorders and motion-related diseases and is expected to reduce pain, increase comfort, increase independence in activities of daily life and relieve a variety of symptoms.

Alternatively, or additionally, it is expected that the various embodiments of the invention described hereinabove will find utility in physical training for sport and/or fitness and/or as part of rehabilitation and/or physiotherapy and/or in an ambulatory or home setting.

Alternatively, or additionally, it is expected that the various embodiments of the invention described hereinabove will provide warnings of excess stress that could lead to injury and/or encourage gait correction and/or provide internal/external stimulation and/or provide biofeedback.

Alternatively, or additionally, it is expected that the various embodiments of the invention described hereinabove will obviate the need for a gait analysis laboratory in some subjects. By doing so it will allow diagnosis and/or monitoring and/or training and/or treating outpatients and/or in various life settings, in real time. Such embodiments can be slipped into everyday use shoes, are lightweight, and inconspicuous.

Alternatively, or additionally, it is expected that the various embodiments of the invention described hereinabove will be provided in the sole of a shoe, as opposed to an insole. According to these embodiments, adjustment includes changes in stiffness of the shoe sole.

Exemplary Data Structures

Referring now concurrently to FIG. 9C and FIG. 4, according to various exemplary embodiments of the invention sensor data signals and/or treatment plan data signals (depicted as double headed arrow in 2412 in FIG. 4) are handled in different ways.

In some embodiments, each of sensors 2112 (FIG. 9C) is provided with a unique identifier (UID). The sensor UID contributes to an ability of system 2400 to distinguish between data output signals from different sensors 2112. Alternatively or additionally, in some embodiments processor 2164 and/or a processor at 2420 stores a map of sensor locations with each sensor UID assigned to a discrete location. The map contributes to an ability of system 2400 to associate data from a specific sensor with a specific location in insole 2410, which corresponds to a matching location on the sole of a foot of user 12010. Alternatively or additionally, in some embodiments system 2400 is provided with a date/time module that associates temporal information with each data output signal from a specific sensor 2112. According to various exemplary embodiments of the invention the date/time module is provided in individual sensors 2112 and/or in processor 2164.

Alternatively or additionally, in some embodiments each of height adjustment mechanisms 2130 is provided with a unique identifier (UID). In some embodiments, a processor at 2420 stores a map of height adjustment mechanism locations with each height adjustment mechanism UID assigned to a discrete location. The height adjustment mechanism UID contributes to an ability of system 2400 to implement a location-based treatment plan.

Regardless of the exact configuration, data output signal 2412 from insole 2410 to a data processor at 2420 carries a bundle of separate signals from different individual sensors 2112, with each individual sensor signal associated with a UID, a physical location within insole 2410 and temporal information. This data is analyzed by the data processor at 2420 which responds by displaying 2412 the data (e.g. as a map) to user 12010 on screen 2422 and/or responds by formulating a treatment plan including instructions for adjustment of individual height adjustment mechanisms 2130. According to some exemplary embodiments of the invention, the treatment plan is displayed 2414 on screen 2422 to user 12010 for manual implementation 2450. In other exemplary embodiments of the invention, the treatment plan is transmitted from 2420 as a digital signal 2412 directly to insole(s) 2410 for automatic implementation. Treatment plan digital signal 2412 carries a bundle of separate implementation signals for different individual height adjustment mechanisms 2130, with each individual implementation signal associated with a UID for a specific height adjustment mechanism 2130.

When treatment plan digital signal 2412 arrives at insole 2410 it is parsed by processor 2164 into individual signals for individual height adjustment mechanisms 2130 using the adjustment mechanism UIDS. In some embodiments, processor 2164 stores a list of UIDS for height adjustment mechanisms 2130.

Exemplary Data Outputs from an Insole

According to various exemplary embodiments of the invention, sensors of one or more types in insoles provide one or more types of data.

In some embodiments, pressure sensors provide output including unique identifier sensor and/or unique identifier insole and/or sensor location and/or pressure (e.g. in N/cm2 or kPa) and/or timestamp.

Alternatively or additionally, in some embodiments, temperature sensors provide output including unique identifier sensor and/or unique identifier insole and/or sensor location and/or temperature and/or timestamp.

Alternatively or additionally, in some embodiments, shear force sensors provide output including unique identifier sensor and/or unique identifier insole and/or sensor location and/or resistive force measurement (e.g. in kPa) and/or timestamp.

Alternatively or additionally, in some embodiments, humidity sensors provide output including unique identifier sensor and/or unique identifier insole and/or sensor location and/or relative humidity (RH) measurement (e.g. in Celsius) and/or measurement resolution and/or timestamp.

Alternatively or additionally, in some embodiments the system records temporal gait characteristics such as heel strike and/or toe-off timing. Alternatively or additionally, in some embodiments accelerometer and gyroscope output allow the system to record Spatial gait measurements such stride length and/or stride velocity and/or Cadence and/or Stance and/or swing duration and/or step duration and/or asymmetry.

Alternatively or additionally, in some embodiments, the system records data for height adjustment mechanisms such as location and/or activity status and/or last height set value and/or new height set value and/or default height value and/or max height and/or min height and/or new adjustment in mm. In some embodiments automated height adjustments mechanisms provide data output signals. In other exemplary embodiments of the invention, the system records data based on the last instruction issued for each height adjustment mechanism, whether the mechanism operates manually or automatically.

It is expected that during the life of this patent many adjustment mechanisms and/or communication protocols will be developed and the scope of the invention is intended to include all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

Exemplary User Interfaces

Figure 12:
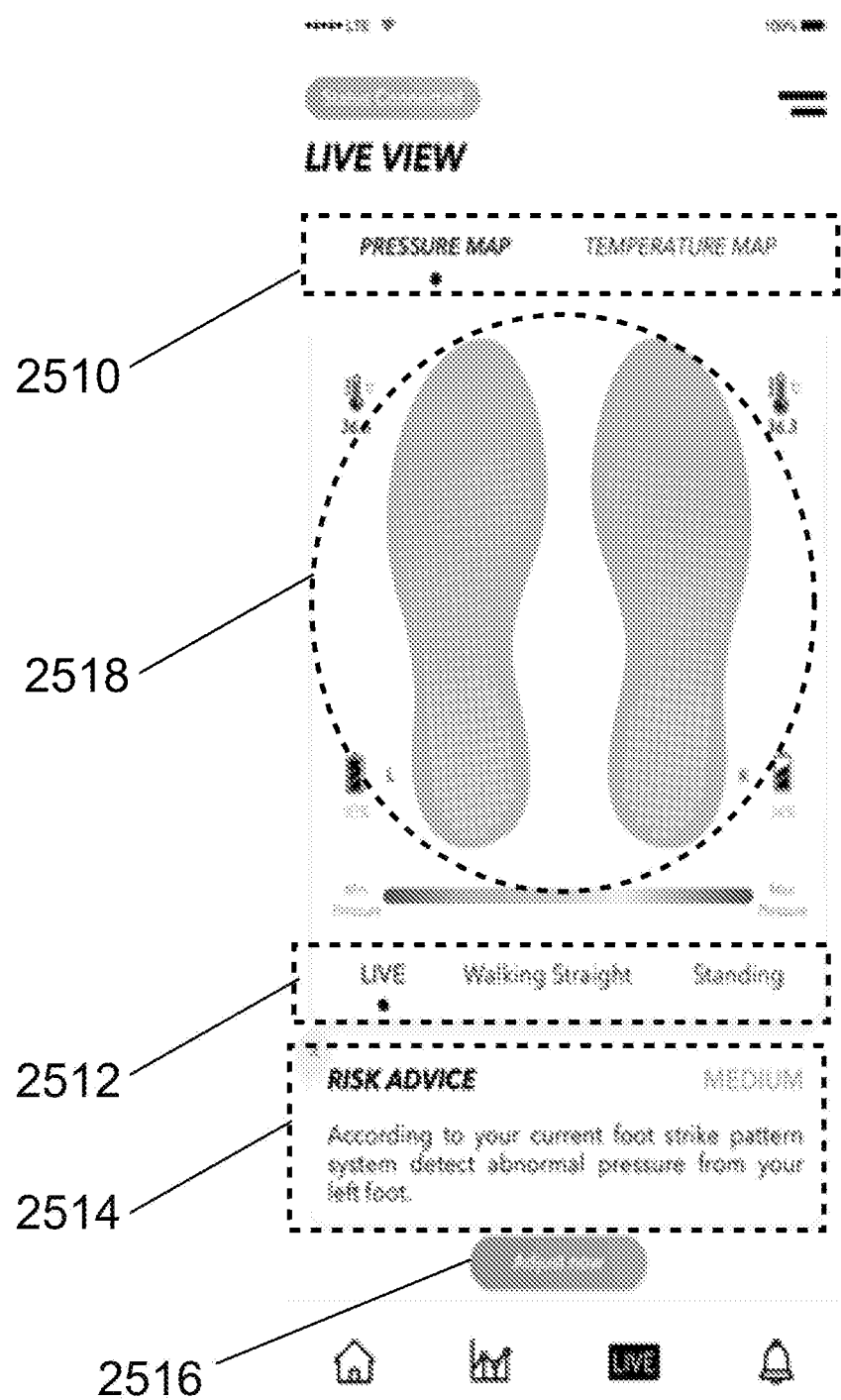
FIG. 12 is a screen shot depicting an exemplary user interface according to some exemplary embodiments of the invention.
Figure 13:
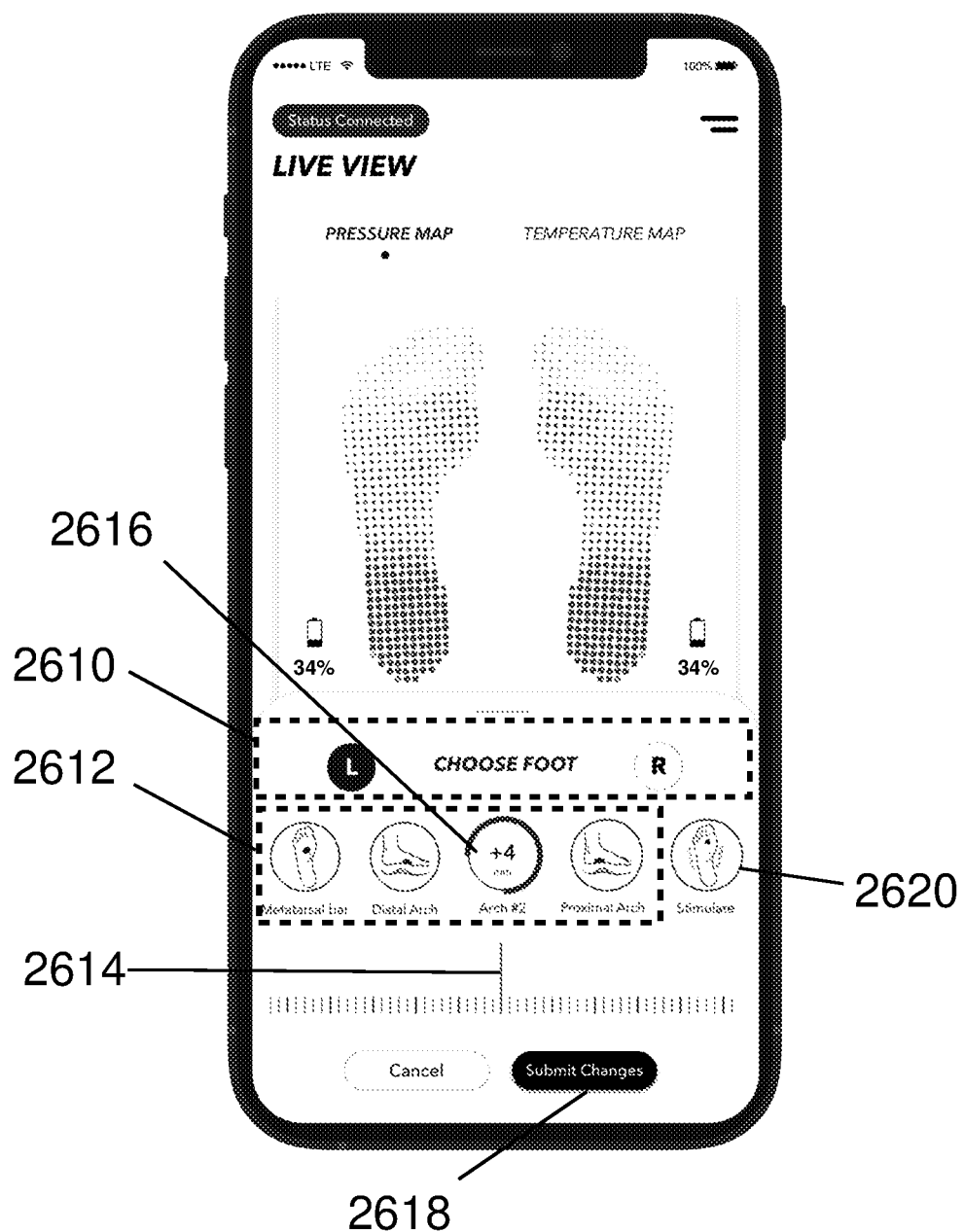
FIG. 13 is a screen shot depicting an exemplary user interface according to some exemplary embodiments of the invention.
Figure 14:
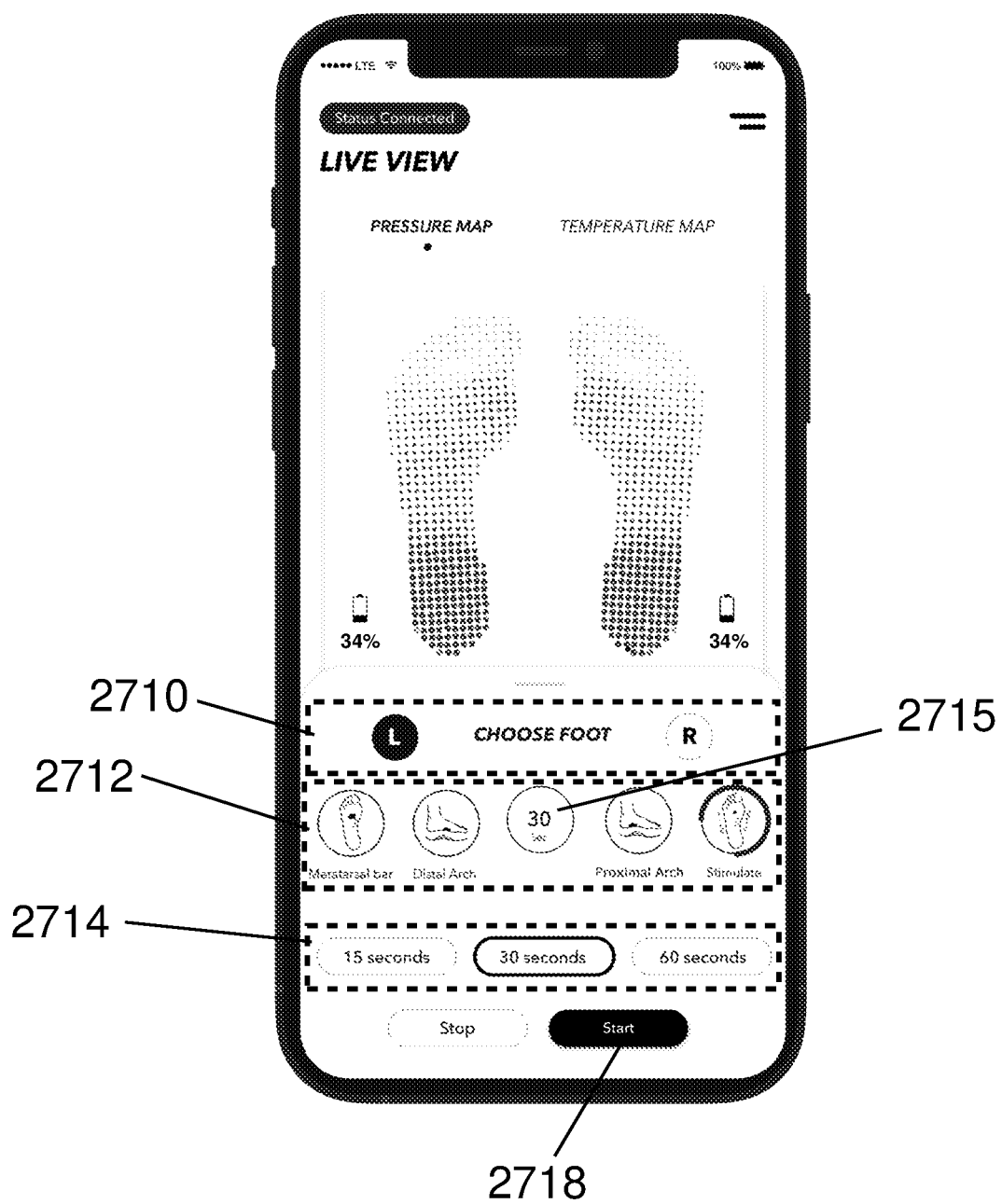
FIG. 14 is a screen shot depicting an exemplary user interface according to some exemplary embodiments of the invention.

FIG. 12; FIG. 13 and FIG. 14 are scree captures depicting exemplary user interfaces associated with operation of a system 2400 as illustrated in FIG. 4.

FIG. 12 is an exemplary main user interface which would is presented when a user 12010 (FIG. 4) logs into an insole management application on device 2420 (FIG. 4). The main user interface has tab bar menu 2510 to select data type to be displayed. In the depicted embodiment, there are tabs for pressure map and temperature map. In other exemplary embodiments of the invention, other types of display may be available, depending on the sensor types deployed in the insole. A second set of tab bar buttons 2512 allows the user select the situation type for which data is to be displayed. The current selection is "live" meaning current sensor output data is displayed in map 2518. In the depicted embodiment, the other available situations are walking straight and standing. In other exemplary embodiments of the invention, situations such as running and stair climbing are presented. Panel 2514 is an alert for user 12010 (see 2414 in FIG. 4). Button 2516 labelled adjust now allows the user to input a command.

FIG. 13 depicts an exemplary popup screen which appears when the user clicks on Adjust now button 2516 from the main screen. The depicted exemplary popup screen includes buttons for controlling the operation of adjustment mechanisms. The depicted exemplary popup screen includes a foot selection menu 2610 for indicating which insole to operate and a target area selection menu 2612 that allows the user to select an area of the foot where height adjustment is to be implemented. In the depicted embodiment, target area selection menu 2612 includes metatarsal bar; distal arch, Arch #2 and proximal arch.

In some embodiments, the user employs slider 2614 to select an amplitude and direction of change which is then displayed 2616 over the relevant foot are in menu 2612. In other exemplary embodiments of the invention, the system indicates the suggested amplitude and direction of change which is then displayed 2616 over the relevant foot are in menu 2612. In either case the user implements the change by clicking submit changes button 2618.

In the depicted embodiment, stimulate button 2620 offers the user the possibility of applying stimulation, either in addition to, or instead of height adjustment.

FIG. 14 depicts an exemplary popup screen which appears when the user clicks on stimulate button 2620.

The depicted exemplary popup screen of FIG. 14 includes a foot selection menu 2710, a target area selection menu 2712 and a duration selection menu 2714. In the depicted embodiment, target area selection menu 2712 includes metatarsal bar; distal arch, and proximal arch (Arch #2 is for illustration purpose). In the depicted embodiment, the time selected at 2714 is superimposed 2715 over the relevant location is menu 2712. In other exemplary embodiments of the invention, the system indicates the suggested location and duration of stimulation which is superimposed 2715 over the relevant location is menu 2712. In either case the user implements the stimulation by clicking start button 2718.

The individual features described hereinabove and presented in examples hereinbelow can be combined in all possible combinations and sub-combinations to produce additional embodiments of the invention. The information given above and in the examples below is illustrative in nature and does not limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively, or additionally, various exemplary embodiments of the invention exclude any specific feature, part, component, module, process or element which is not specifically disclosed herein.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Additional objects, advantages, and novel features of various embodiments of the invention will become apparent to one ordinarily skilled in the art upon examination of the following examples, which are not limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Young Athlete

A 20-year-old male (e.g. user 12010 in FIG. 4) of good physical condition except minor flat feet in both legs will run on a level surface. Data will be collected using sensors in insoles 2410 and an initial diagnosis will be made.

According to various exemplary embodiments of the invention the diagnosis is made by a data processor smartphone 2420 and/or by a remote analytic module in cloud 2430 and/or with input from a healthcare specialist 12020 via computer 2440. Based on this diagnosis it will appear that the insoles provide sufficient support so no change will be implemented in the insoles. The system will set an individual threshold for a follow-up analysis (if one or more parameters are met or exceeded; not necessarily a full analysis) based upon personal data and observed history. For example, in some embodiments the systems sets a threshold of 200 kPa for vertical plantar pressure and/or a threshold of temperature increase of more than 2.2 Celsius.

Parameters and values for thresholds are described in, for example "The role of foot pressure measurement in the prediction and prevention of diabetic foot ulceration—A comprehensive review" (Chatwin et al. (2019) Diabetes Metab Res Rev 36(4):e3258 and/or in Beach, Christopher & Cooper, Glen & Weightman, Andrew & Hodson-Tole, Emma & Reeves, Neil & Casson, Alex. (2021) "Monitoring of Dynamic Plantar Foot Temperatures in Diabetes with Personalized 3D-Printed Wearables Sensors" (Basel, Switzerland). 21. 10.3390/s21051717; each of which is fully incorporated herein by reference).

In this example, Vertical Foot Pressure will be measured by Force sensing resistors (FSR) or a Pressure Sensor Matrix from a conducted fabric such as VELOSTAT or by sensors based on graphene hybrids.

In this example the pressure sensors will gather cumulative pressure data and/or peak pressure data and/or Pressure-time integral data. Alternatively or additionally, in this example gait analysis during activity will be generated from accelerometer and/or gyroscope data. In some embodiments, the system algorithm will compare the peak plantar foot pressure data, gait parameters, and the pathway of the center of pressure (COP) between a normal foot model and the patient's feet. If this comparison will indicate an over-threshold pressure which affects the COP and/or a significant change of gait parameters then the system generated diagnosis will indicate a flat foot and according to comparison between the current foot pressure distribution map versus normal foot pattern model, the algorithm will decide on which adjustment mechanisms should be activated and the rates and/or magnitudes of adjustments. (see for example Huang et al., PLoS One (2020)15(8): e0237382. doi) "The arch support insoles show benefits to people with flatfoot on stance time, cadence, plantar pressure and contact area" and/or Han et al., (2011) Journal of Physical Therapy Science 23(4):683-685 "Differences in Plantar Foot Pressure and COP between Flat and Normal Feet During Walking"; each of which is fully incorporated herein by reference)

As an example, after 15 minutes of running and additional distance of 2.5 km an additional system 200 will recalculate as a result of reaching the individual threshold. This recalculation will identify stress and increase of plantar pressure in the left foot in the region of the arch, and foot joint motion parameters. The system will decide that the stress has caused a risk of injury to the user as a result of improper foot placement during his activity. The algorithm will calculate that providing additional support in the arches region for both feet will improve user's biomechanics and/or balance and/or motion. This calculation will be done by AI and/or ML algorithms implemented at 2420 and/or 2430. s. In this case, the autonomously generated treatment plan will include increasing the height of proximal left arch area of insole by 3 mm and by 5 mm to the right medial arch area of insole.

In some embodiments, the sensor data will be gathered and stored in a DB (e.g. 720 in FIG. 7) and the algorithm will calculate a treatment plan according to a set of clinical roles and comparison between various known clinical foot patterns, a recognition for analysis using machine learning (ML)— or other forms of pattern for DFU prediction or treatment.

According to a human gait DB (e.g., digital medical records stored at 720 in FIG. 7) that will be trained using artificial intelligence (AI) and/or ML algorithms, the system's ability to diagnose patients and/or formulate treatment plans will improve over time as a number of records in the DB (e.g. 720) increases.

Alternatively or additionally, sensor output data will be visualized to maps so health care specialists can train the ML algorithm about the treatment plan and/or changes/adjustments that should be implemented.

In some exemplary embodiments of the invention, this treatment plan will be sent as a digital instruction 2412 (e.g. via Bluetooth 2416) from smartphone 2420 to insoles 2410. According to these embodiments, digital instruction 2412 is parsed by a processor in insoles 2410 to separate digital signals for each individual height adjustment mechanism in insoles 2410 and each individual height adjustment mechanism responds to the digital signal it receives automatically. In some exemplary embodiments of the invention, changes in height adjustment mechanisms will take place when the foot has minimum force exerted on it, for example when the foot is in the air in motion. Alternatively or additionally, in some embodiments a change to a height adjustment mechanism will be implemented incrementally over time.

In other exemplary embodiments of the invention, this treatment plan is provided to user 12010 as user advice 2414 on a display 2422 of smartphone 2420. User 12010 then manually implements 2450 the treatment plan by adjusting each height adjustment mechanism in insoles 2410 manually In some embodiments, user advice 2414 on display 2422 will instruct user 12010 with a bottom insole map for each foot with visual guidance to the exact location of adjustment mechanism(s) and the rate of change and/or magnitude of change. Each adjustment mechanism will be numbered and a visual and/or sound indicator for the grade of change (e.g. for each 1 mm of change user will feel click while he turns).

After implementation of the treatment plan evaluation(s) as described above will indicate treatment plan efficacy. If necessary, a supplementary treatment plan will be formulated and implemented as described above. The cycle will then be repeated periodically and/or in response to threshold triggers.

Example 2

Diabetic Male

In a male diabetic subject aged 49 with no signs (or early signs of neuropathy), it is hard to diagnose accurately or predict the risk of diabetic foot ulceration, especially for those with poor self-care management. The system will measure patient compliance (e.g., hours/day insole used) and monitor the clinical metrics needed by the healthcare specialist 12020 (FIG. 4) to manage the patient, remotely, in patient's day to day activities.

In this example the relevant main clinical metrics will be plantar pressure data and/or dynamic foot temperature parameters in various sites and/or gait metrics are the main clinical metrics. Supportive clinical indicators such as plantar shear stress (friction) distribution data and plantar foot humidity in various sites will also be used in some embodiments.

Healthcare specialist 12020 will access data through a dedicated secured network portal (e.g. at 2440). System 2400 will collect, analyze and display output from sensors in insoles 2410, including historical sensor output data, of that patient for the healthcare specialist 12020. Cumulative output from sensors in insoles 2410 will assist healthcare specialist 12020 to detect and address inflammation before actual formation of diabetic foot ulcers (DFUs). This early detection will contribute to a reduction in the risk of amputation. According to these embodiments, insoles 2410 will be embedded with a multitude of sensors that will measure and detect differences in real time of stress and/or pressure and/or foot temperature and/or shear forces and/or humidity and/or climate of the foot. In some embodiments, climate of the foot will be measured by one or more Microclimate Sensor Arrays capable of measuring microclimate including temperature, pressure and humidity.

In some embodiments sensor data output 2412 relayed to a data processor of smartphone 2420 will trigger an alert to the patient 12010 and/or the healthcare specialist 12020 if a trigger threshold is exceeded.

In some embodiments, the Peak pressure threshold (maximum physical force exerted on a region) will be 200 kPA. Alternatively or additionally, in some embodiments the temperature threshold will be a 2.2° C. increase. Alternatively or additionally, in some embodiments temperature asymmetry measurements between feet and/or combining both contralateral and mean temperature analysis will serve as temperature thresholds.

Shear stresses occur when two forces exert in opposing directions causing a deformation of the tissue parallel to that surface. Subsequent research suggests that local peak shear stress is higher in patients with diabetes (mean 82.0±26.4 kPA) than healthy controls (64.6±15.7 kPA), and higher still in those with diabetic neuropathy (86.4-91.3±29.0-30.3 kPA) and in people with a history of DFU neuropathy (135.3±60.6 kPA) (Jones et al., "Prediction of Diabetic Foot Ulceration: The Value of Using Microclimate Sensor Arrays" (2020) J Diabetes Sci Technol 14(1):55-64; which is fully incorporated herein by reference).

In some embodiments, humidity sensors and/or mean skin resistance (which indicates a level of hydration) will be employed. Both a lack of moisture and excess moisture can affect foot health, especially for diabetic neuropathic patients. Despite the studies about the correlation of DFU and foot humidity there is no characterized clinical threshold. Insoles according to exemplary embodiments of the invention provide an important tool for data gathering and correlation of data with disease progression and/or treatment outcomes.

In some embodiments the threshold is set individually for the specific patient 12010. In some embodiments healthcare specialist 12020 will decide whether to summon patient 12010 to the clinic and/or to provide a treatment plan.

If healthcare specialist 12020 provides a treatment plan, it will be implemented either manually or automatically as described in Example 1.

In some embodiments, data will be presented to healthcare specialist 12020 in the form of, for example, a temperature map and/or a pressure map. In some embodiments healthcare specialist 12020 will compare data over a period of time to identify a trend and to diagnose. In therapeutic plantar pressure off-loading the system will minimize or remove weight which will be placed on the foot to help prevent and heal ulcers, particularly those caused by poor circulation to the feet and to avoid dangerous secondary infections which are indicators of inflammation that could lead to debilitating foot ulcers and even amputation. For example, if there is an ulcer, or risk of an ulcer under the metatarsal heads of the foot, height adjustment mechanisms in the midfoot part of the foot, before the vulnerable sites and/or arch site will be raised even more from the top surface of the insole so that the metatarsal head is suspended above the insole surface in a way that will reduce plantar pressure over at risk sites by redistributing pressure across other areas (increasing total contact area) of the foot (within safe limits). Evaluations show that a custom-made foot orthotic can increase total contact area (redistribute force) and is able to reduce plantar pressures. Thus, an insole according to an exemplary embodiment of the invention should reduce the risk of ulceration in the diabetic neuropathic foot.

According to this embodiment, as long as insoles 2410 will be worn, the sensors will monitor foot health. In some embodiments a treatment plan implemented by system 2400 will include activation of a stimulating mechanism (see 539 in FIG. 5B) to improve neural sensitivity of the plantar. In some embodiments external monitoring device (e.g. smartphone 2420) will alert user 12010 or a healthcare specialist 12020 about detection of abnormal pressure and DFU potential risks. According to these embodiments, treatment and/or response plan will be activated automatically, by user and/or remotely by a health professional.

In some embodiments, user 12010 will manually activate 2450 the stimulating mechanism in insole 2410. In some embodiments, this manual activation will be initiated by the user in response to medical advice 2414 provided by the system. In other exemplary embodiments of the invention, a data processor of phone 2420 will send a signal 2412 to insoles 2410 to activate the stimulating mechanism in response to sensor output data 2412. In either case, the stimulation mechanism will help in diagnosis and/or treatment and/or rehabilitation of neuropathic diabetic patients and/or neuro muscular malady patients and/or post stroke patients. In some embodiments, the stimulation mechanism employs transcutaneous electrical nerve stimulation and/or functional electrical stimulation (FES). Alternatively or additionally, in some embodiments the stimulation mechanism will function to provide foot EMG biofeedback and/or other biofeedback to assist patients 12010 without foot pathologies perform foot doming exercises.

In some embodiments, the diagnosis and treatment will be determined by be decided by health care specialist 12020 at a clinic with physical examination of the foot and done with manual adjustments on the spot. Alternatively or additionally, in some embodiments digital assessment based on sensor data 2412 will aid the decision-making process and/or contribute to the nature of the treatment plan at the discretion of specialist 12020. Alternatively or additionally, the treatment plan can also be decided by specialist 12020 via a dashboard presented as a user interface (UI) at 2440. According to these embodiments, specialist 12020 will send a digital treatment plan across network 2418 to phone 2420 which will relay it to insoles 2410 as treatment plan 2412.

Example 3

Years Old Female Prescribed for Custom Orthotics

A 35-year-old with instabilities and/or gait problems caused by high arches in her feet contributing to lower limb pain will be fitted with insoles 2410 (FIG. 4). Height adjustment mechanisms in insoles 2410 will redistribute the pressure on her feet and/or provide support.

Fitting insoles 2410 will be simple and performed in one clinic visit by selecting an off the shelf product with a suitable shoe sizing. Pairing to a smart device (e.g. phone 242) via Bluetooth 2416 will be conducted during the visit. Once the initial setup process is done and the patient 12010 will start to walk, sensor output data 2412 will be transmitted from insoles 2410 to smartphone 2420. A data processor in 2420 will analyze the sensor output data to complete a 'foot ID' based on gait metrics and/or medical analysis and/or sensor data.

"Medical Analysis" indicates an initial clinical judgment when the patient is prescribed with insoles, foot shape and initial personal medical condition that asses risk for patient. if a patient already had DFU episode in the past and/or their BMI.

"Gait metrics" are derived from movement analysis using accelerometer and gyroscope data outputs. Gait metrics include kinetic and gait parameters such as stance, cadence, balance, step length (r/l), each of which can be plotted as a function of time and co-displayed on the same timeline.

Sensor data includes but is not limited to data output signals from pressure sensors and/or temperature sensors and/or shear force sensors and/or humidity sensors, The sensor data contributes to medical analysis and predictions for patients at risk of ulceration. Pressure sensor data is useful for all kind of patients The foot ID based on gait metrics and/or medical analysis and/or sensor data comprises a 'map' for a clinical diagnosis In some embodiments device 2420 relays data to digital medical records (DMR) (e.g. in cloud 2430 and/or at remote server 2440). According to these embodiments the DMR can be retrieved for further analysis and/or investigation.

Alternatively or additionally, in some embodiments a treatment plan will be prepared by a data processor(s) at 2420 and/or 2430 and/or 2440, optionally with input from healthcare specialist 12020 as described in Example 1. As described in Example 1, the treatment plan will be implemented either manually or automatically.

In this example pressure sensors, accelerometer and gyroscope will be used to extract gait data and find the average peak pressure and if patient cross a certain predetermined threshold. The analysis using machine learning algorithms and deep learning will try to find a recognized pattern in the platform's DB (e.g. 720) that holds the appropriate treatment plan for the problem, alerts the specialist 12020 and/or the patient 12010, and if there is permission, will also implement the treatment plan in a completely autonomous manner.

Example 4

Diabetic Neuropathic Female with Foot Deformity

High blood sugar levels over the years in diabetic patients lead to a progressive damage to nerve fibers and blood vessels, causing peripheral neuropathy and peripheral vascular disease (PVD), respectively. These two conditions are common in diabetic patients. In a female diabetic subject aged 54 insoles 2410 (FIG. 4) will be able to provide physical stimulation and/or laser and/or vibration and/or functional electronic stimulation to the feet (e.g. stimulation modules 539 in FIG. 5B).

Due to neuropathy, the damaged motor nerves lead to atrophy and weakness of the intrinsic foot muscles. In some embodiments, this stimulation will be used as a diagnostic too assess nerve damage and/or progress of nerve damage. Alternatively or additionally, in some embodiments the stimulation will be used to improve balance and/or stability and/or blood flow to the foot and related nerves.

Neuropathy can progress over time and is associated with loss of sensation in the feet. In some embodiments, response of patient 12010 to stimulation will be used to detect and/or measure loss of sensation over time (e.g. test with different low level electrical stimulations to foot) and/or to treat to weakened, damaged or paralyzed muscles. In some embodiments, Transcutaneous Electrical Nerve Stimulation (Tens) will help in the last wound healing stage of ulceration among diabetic foot patients.

Alternatively or additionally, height adjustment mechanisms will play a part in an offloading treatment plan when high pressure and/or high temperature indicative of a pre-ulceration stage appear. In this way, exemplary embodiments of the invention will play a role in prophylactic treatment of diabetic foot ulcers.

In summary, physical stimulation is not part of an offloading treatment plan but an alternative or supplementary treatment plan or assessment tool.

This patient will receive a physical stimulus. According to various exemplary embodiments of the invention the physical stimulus will encourage healing and/or will slow down malady progression. Alternatively or additionally, in some embodiments the physical stimulus will administered as part of an out of lab examination. Alternatively or additionally, in some embodiments the physical stimulus will serve as an assessment tool for a decision maker (e.g. healthcare specialist 12020).

In addition to the damaged motor nerves of this patient, the chronic hyperglycemia limits the joints' mobility and cause a reduction in the tissue's elasticity. These factors combined lead to a rigid and unstable foot with altered weight bearing areas and walking pattern. This increases plantar pressures which can lead to DFU formation. Furthermore, the loss of protective sensation, due to the damage to sensory nerves, also contributes to the increase in plantar pressure. For example, a healthy person feels discomfort after standing for too long and changes positions, shifting the applied pressure to other areas of the feet. However, to our neuropathic female in the example, such discomfort is not felt and pressure continues being applied in the same area for a long period of time, contributing, in the long run, to foot ulceration. Additionally, the damage to the autonomic nerves causes a reduction or elimination of sweating which can be monitored and diagnosed by humidity and/or climate sensors in insoles 4210.

In addition, implementation of a treatment plan based on pressure sensor data will reduce pressure in an area where a pressure sore is developing and/or by adding additional support to deformed areas. According to various exemplary embodiments of the invention implementation of the treatment plan from 2420 and/or 2430 will be implemented manually or automatically as described in Example 1.

Additional support will be provided by an offloading treatment plan in which pressure is eased in peak pressure sites and redistributed to other areas. This will happen as the adjustment mechanisms alter the shape of insoles 2410 by increasing or reducing the total contact area of the foot with the insole. The additional support will not increase pressure but will relieve pressure in problematic areas since it will increase height in surrounding areas (within predefined safe limits). In this way contact of the insole with the originally detected increased pressure area will be reduced and therefore there is almost no pressure on the originally detected increased pressure area once the treatment plan is implemented.

In this example, subject 12010 is diagnosed with Charcot, so clinical offloading treatment will be via adding more height adjustments of insole surface in the medial arch and/or the navicular area (e.g. from 20 mm to 30 mm). The data collected will also be accessed by patient 12010 and shared with family members, healthcare specialist 12020, or others in order to determine if a surgical intervention or other treatment is needed.

Example 5

Flat Feet Amateur Male

A male subject aged 33 who suffers from a mild deformation of foot and has never been diagnosed or prescribed with custom orthotics will use his smart device (e.g. smartphone 2420 (FIG. 4) or smartwatch) to pair (e.g. via Bluetooth 2416) to insoles 4210. Following instructions on screen 2422 user 12010 will perform a gait and balance evaluation which will be analyzed. In this case a slight overpronation of his right foot and a moderate overpronation of his left foot will be diagnosed. Because the severity of the problem is different in each foot, the system will operate differently for each foot but will maintain proper mobility and balance overall. The system will use the paired smart device to prepare and execute an automated corrective and/or therapeutic response plan as described in Example 1.

Sensor data from insoles 4210 will be used to generate a pressure map of each foot. A gait pattern will be compared to personal data parameters such as age, weight, and height of user. The comparison and evaluation are based on proper clinical and biomechanical guidelines to find differences and asymmetry in gait pattern and areas in the foot where there is increased pressure above average.

The gait pattern will be derived from accelerometer data and gyroscope data which provide information about movement and orientation in space. An array of force sensors will concurrently detect plantar pressure. Measurements will be made at the rate of hundreds per seconds in real time and in different gait tests in the real world (e.g. walking on a level straight line for short period time, climbing stairs, walking uphill). The measurements data from a few features will be processed by an algorithm (e.g. AI) to rapidly can rapidly extract gait parameters such as stride velocity, swing, and duration and/or detect temporal events. According to various exemplary embodiments of the invention the algorithm runs on a data processor in insoles 2420 (and/or 2440) and/or on a data processor in linked device 2420 and/or in cloud 2430. For example, data from pressure sensors in insoles 2410 will be used by the algorithm to identify gait phases such as heel strike and/or toe off. The processed data will be stored as a gait analysis and/or clinical evaluation.

In some embodiments, database 720 (FIG. 7) will reside in in platform cloud 2430. This database will update over time with many kinds of human gait analysis, which will be gathered under different real-life settings using insoles 2410 according to an embodiment of the invention. The database will also store clinical data regarding pathological patterns and potential risks which will be provided to the AI algorithm to search for according to patient's demographic and/or clinical data such as BMI and/or DFU history and/or foot conditions (e.g. flat foot or pronation) and/or lower limb conditions. According to similar patterns already identified and flagged as successful treatment done in similar patients using insoles 2410, system 2400 will be able to quickly recommend a treatment plan with a high success probability. The algorithm will take into consideration user feedback on results of an initial treatment plan and/or temporally relevant sensor data in formulation of updated treatment plan. In this way, system 2400 will adapts itself according to the needs, foot condition and ability of patient 12010.

According to various exemplary embodiments of the invention implementation of the treatment plan will be manual or automatic as described in Example 1. System 2400 will continue to monitor the user's gait and balance, in different life settings, in real time, and will provide a new improved solution of adjustment when needed. For example, if the user replaces or switches to different shoes the system will dynamically adjust insoles 4210 to improve fit and support of each foot by adjusting heights in vertical direction.

Example 6

Diabetic Patient at Risk for Foot Ulcer Recurrence

Diabetic foot ulcers (DFUs) are associated with increased morbidity, mortality, and resource utilization. A 50-year-old diabetic patient has DFU history so he is at high-risk to develop a diabetic foot ulcer. The currently available standard of care does little to prevent incidence and recurrence of foot ulcer. One reason for this is that measurement of patient compliance to a treatment plan is difficult. The various exemplary embodiments of the invention will facilitate monitoring DFU related risk factors on a daily basis. This will contribute to empowerment of patients in self-care and/or engage patients to use insoles 2410 to effectively coordinate care with specialists 12020.

Patient 12010 will be prescribed insoles 4210 (FIG. 4) for daily use with telemedicine support from healthcare specialist 12020. Insoles 4210 will have sensing and monitoring components as described hereinabove. Insoles 4210 will output sensor data 2412 to data processor(s) at 2420 and/or 2430 and/or 2440. These data processors will generate reports and/or a treatment plan.

The objective for this patient is early inflammation detection. Temperature data will be collected by temperature sensors in insole 2410 and automatically analyzed for temperature differences, or asymmetry, between the left and right feet at different locations such as: heel; arch; first, third, and fifth metatarsal heads; and the hallux.

For example, if this patient is with temperature asymmetry exceeding a 2.2° C. threshold over two or more consecutive uses at the same location, insole 4210 will send an alert 2414 to the patient (12010) and/or to the healthcare specialist 12020. After issue of alert 2414 the patient will be considered to be in episode. If patient 12010 is also with a pressure peak, at the same location, exceeding the average pressure according to patient's history, this strengthens the clinical diagnosis of inflammation preceding a DFU at an average of weeks prior to clinical presentation. The system can decide to monitor this patient more aggressively and flag at high risk. Health care specialist 12020 can decide how to proceed with care and/or use telemedicine capabilities to send a personalized offloading treating plan and/or the system insole can autonomously decide and initiate, based on predictive AI algorithms, an effective prevention of DFU protocol with noninvasive intervention pressure offloading plan according to an exemplary embodiment of the invention.

When a digital customized offloading treatment plan is initiated, insole 2410 will dynamically adjust its shape by changing vertical heights at various coordinates of the insole in order to reduce pressure from the problematic foot site. The calculation of this personalized offloading is based on past and current clinical data gathered from sensors (e.g. temperature map, pressure map, humidity of foot, gait) and de-identified in accordance with best practices and other similar events indexed in platform. Data will be saved and accumulated in the long-term to improve clinical decision making. So, in this example for this patient with a history of DFU under the 2nd metatarsal and based on current sensory diagnosis of inflammation at the same area of foot, the system initiates an offloading plan which will actively reduce pressure (and therefore temperature) from the problematic area site of our patient by raising the adjacent areas so that when stepping on the foot will not apply load in the same area. The dynamic offloading of insole goes into action when the insole feels that there are minimum to no forces exerted on it (e.g. While walking in the part where the foot is in the air).

In some embodiments, system 2400 will provide an autonomous feedback loop for prophylactic treatment of DFU by automatically formulating and implementing a treatment plan in response to data output signals from sensors in insole 2410.

The invention claimed is:

1. A system configured to provide early diagnosis, evaluation, and therapeutic measures for chronic foot maladies and pains, said system comprising:
   (a) an insole comprising:
      i) a plurality of height adjustment mechanisms deployed thereupon at a plurality of locations; wherein each height adjustment mechanism in said plurality of height adjustment mechanisms is provided with a unique identifier; and
      ii) a plurality of sensors deployed thereupon at a plurality of locations;
   wherein, each sensor in said plurality of sensors is provided with a unique identifier and is configured to provide a data output signal;
   (b) a data processor that comprises at least one software algorithm configured to receive said data output signal from at least one sensor in said plurality of sensors; wherein each data output signal from each of said sensors in said plurality of sensors is associated with said unique identifier of said sensor in said plurality of sensors, a physical location within said insole, and temporal information; and to analyze data from said data output signals from said sensors in said plurality of sensors, and provide a response plan; and
   (c) the response plan is configured to be compatible with at least one of:
      (i) an autonomous implementation module configured to autonomously receive said response plan, to translate said response plan into a bundle of separate implementation signals, wherein each of said separate implementation signals is associated with said unique identifier of each of said height adjustment mechanisms in said plurality of height adjustment mechanisms; and to transmit each separate implementation signal of said bundle of separate implementation signals to said height adjustment mechanism in said plurality of height adjustment mechanisms that has said unique identifier that is associated with said separate implementation signal;
      (ii) a healthcare professional that is trained to receive said response plan, translate said response plan to a plurality of separate implementation signals, wherein each of said separate implementation signals in said bundle of separate implementation signals is associated with said unique identifier of each of said height adjustment mechanisms in said plurality of height adjustment mechanisms, to transmit each of said separate implementation signals in said bundle of separate implementation signals to said height adjustment mechanism in said plurality of height adjustment mechanisms that has said unique identifier that is associated with said separate implementation signal, and to automatically activate said height adjustment mechanism in said plurality of height adjustment mechanisms; and (iii) a data processor configured to formulate a treatment plan including instructions for adjustment of said height adjustment mechanisms in said plurality of said height adjustment mechanisms and displaying the treatment plan on a screen for manual implementation;

said system characterized in that:

(A) each of said height adjustment mechanisms in said plurality of said height adjustment mechanisms is configured to be activated to increase or decrease its height, thereby changing the height of the insole at the location of said height adjustment mechanism;

(B) activating at least two of said height adjustment mechanisms from said plurality of height adjustment mechanisms alters the surface of said insole thereby enabling off-loading;

(C) said insole is configured to be slipped into everyday use shoes, thereby allowing at least one of: diagnosis, monitoring, training, and treating outpatients in various life settings, in real time; and (D) said unique identifiers of each of height adjustment mechanisms in said plurality of height adjustment mechanisms and said unique identifiers of said sensors in said plurality of sensors allow said system to be configured to be integrated with a mobile phone and a remote monitoring platform.

2. The system according to claim 1, wherein said data processor is located in at least one or more members of the group consisting of: in the insole, on the insole, configured to be worn by a user of the insole, configured to be carried by a user of the insole, and at a remote server.

3. The system according to claim 1, wherein each of said height adjustment mechanisms in the plurality of height adjustment mechanisms includes at least one member of the group consisting of: pistons, piezoelectric materials, motors, gears, bevel gears, worm-drive gears, screws, spring loaded mechanisms, hydraulic actuators, stimulators, polymers, and electroactive materials.

4. The system according to claim 1 wherein said processor is configured to automatically track gait behavior, physiological activities and plantar parameters of said user to generate at least one of a prediction of risk and an alert concerning at least one of gait abnormalities and foot pathologies.

5. The system according to claim 1, comprising a stimulation module under control of said implementation module, wherein said response plan includes a stimulation signal; said system characterized in that said response signals are configured to activate said stimulation module to perform at least one of the following: manage pain, aid circulation, improve gait impairments, and provide therapeutic measures for a patient.

6. The system according to claim 5, wherein said stimulation module includes at least one member of the group consisting of: a physical stimulator, a laser, a vibrator, and a source of electric current.

7. The system according to claim 1 wherein:

(a) at least one sensor of said plurality of sensors is configured to produce time stamped data output signals labeled with UIDs (unique identifiers) for users; and (b) said data processor comprises a database configured to receive and store said time stamped data output signals labeled with UIDs.

8. The system according to claim 1, wherein at least one of said data processor or said implementation module comprises at least one of: artificial intelligence algorithms or machine learning algorithms that are configured to improve the system's ability to do at least one of the following: provide feedback, diagnose patients, and formulate treatment plans.

9. The system according to claim 1 comprising:

(a) a user interface (UI) configured to receive user input defining a problem area on a sole of a foot; and (b) said processor comprises a translation module configured to translate said user input into a response signal; said system characterized in that said response signal activates each height adjustment mechanism in said plurality of height adjustment mechanisms that is located at said problem area to alleviate the problem in said problem area.

10. An insole comprising:

(a) a plurality of manual height adjustment mechanisms integrated across at least a portion of an area of said insole; and (b) a manual adjustment interface for each manual height adjustment mechanism in said plurality of manual height adjustment mechanisms;

said insole characterized in that:

(A) each of said manual height adjustment mechanisms in said plurality of manual height adjustment mechanisms is provided with a manual adjustment interface thereby allowing each of said manual height adjustment mechanisms in said plurality of manual height adjustment mechanisms to be activated independently of all other manual height adjustment mechanisms in said plurality of manual height adjustment mechanisms in order to change the height of the insole only at the location of said manual height adjustment mechanism;

(B) said plurality of manual height adjustment mechanisms are configured to alter the surface of said insole and to enable off-loading treatment; and (C) said insole is configured to be slipped into everyday use shoes, thereby allowing at least one of: diagnosis, monitoring, training, and treating outpatients in various life settings, in real time.

11. The insole according to claim 10, wherein each of said manual height adjustment mechanisms in said plurality of manual height adjustment mechanisms is independently selected from the group consisting of: a screw, a diagonal joint rotary lift, and a bayonet mount.

12. The insole according to claim 10, comprising one or more sensors.

13. The insole according to claim 10, comprising a stimulation module and an activation interface for said stimulation module.

14. The insole according to claim 13, wherein said stimulation module includes at least one member of the group consisting of: a physical stimulator, a laser, vibrator and a source of electric current.

15. A system configured to provide to early diagnosis, evaluation, and therapeutic measures for chronic foot maladies and pains, the system comprising:

(a) one or more insoles comprising:
- (i) plurality of manual height adjustment mechanisms integrated across at least a portion of an area thereof;
- (ii) a manual adjustment interface for each manual height adjustment mechanism in said plurality of manual height adjustment mechanisms; and
- (iii) one or more sensors in said one or more insoles, said one or more sensors configured to provide one or more output signal(s);

(b) wherein said one or more output signals are configured to be compatible with at least one of:
- (i) a data processor that is designed and configured to translate said output signal(s) to user advice;
- (ii) a healthcare professional that is trained to translate said output signal(s) to user advice; and (c) an interface configured to present said advice; said system characterized in that:
- (A) each one of said manual height adjustment mechanisms in said plurality of manual height adjustment mechanisms is configured to change the height of the insole at the location of said manual height adjustment mechanism;
- (B) said plurality of manual adjustment mechanisms is configured to customize the surface of said insole; and
- (C) said user advice is configured to include instructions to a user for manual adjustment of said manual height adjustment mechanisms in said plurality of manual height adjustment mechanisms in said insole; and
- (D) said insole is configured to be slipped into everyday use shoes, thereby allowing at least one of: diagnosis, monitoring, training, and treating outpatients in various life settings, in real time.

16. The system according to claim 15, wherein said user advice comprises a set of instructions for manual adjustment of said manual height adjustment mechanisms in said plurality of manual height adjustment mechanisms.

17. The system according to claim 15, wherein said data processor is configured to automatically track gait behavior, physiological activities, and plantar parameters of said user to generate at least one of a prediction of risk and an alert concerning at least one of gait abnormalities and foot pathologies.

18. The system according to claim 15, comprising:
- a stimulation module in each of said one or more insoles; and
- a manual activation interface for each one of said stimulation modules;
- wherein said stimulation modules include at least one member of the group consisting of:
- a physical stimulator, a laser, a vibrator, and a source of electric current.

19. The system according to claim 15, wherein said data processor is located in at least one or more members of the group consisting of: in the insole, on the insole, configured to be worn by a user of the insole, configured to be carried by a user of the insole, and at a remote server.

20. The system according to claim 19 comprising:
- (a) a user interface (UI) configured to receive user input defining a problem area on a sole of a foot; and
- (b) said data processor comprises a translation module configured to translate said user input into a response signal.

* * * * *